US008143003B2

(12) United States Patent
Inazawa et al.

(10) Patent No.: US 8,143,003 B2
(45) Date of Patent: Mar. 27, 2012

(54) METHOD FOR DETECTING ORAL SQUAMOUS-CELL CARCINOMA

(75) Inventors: Johji Inazawa, Tokyo (JP); Issei Imoto, Tokyo (JP); Erina Nakamura, Tokyo (JP); Hitoshi Tsuda, Tokyo (JP)

(73) Assignees: Fujifilm Corporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 243 days.

(21) Appl. No.: 12/430,639

(22) Filed: Apr. 27, 2009

(65) Prior Publication Data

US 2010/0035758 A1 Feb. 11, 2010

(30) Foreign Application Priority Data

Aug. 8, 2008 (JP) ................................ 2008-205138

(51) Int. Cl.
*C12Q 1/68* (2006.01)

(52) U.S. Cl. ........................................................ 435/6.1

(58) Field of Classification Search ........................ None
See application file for complete search history.

(56) References Cited

OTHER PUBLICATIONS

Tockman et al (Cancer Res., 1992, 52:2711s-2718s).*
Nakamura et al (Cancer Sci, 2008, 99(7): 1390-1400).*
Gunn et al (American Journal of Medical Genetics, 2003, 120A: 127-135).*

* cited by examiner

*Primary Examiner* — Sean Aeder
(74) *Attorney, Agent, or Firm* — Birch, Stewart, Kolasch & Birch, LLP

(57) ABSTRACT

It is an object to be achieved by the present invention to provide a method for detecting cancer and a cell growth inhibiting agent by the identification of genes exhibiting characteristic behavior in cancers such as oral squamous-cell carcinoma. The present invention provides a method for detecting cancer, which comprises detecting at least one gene alteration existing in chromosomal region 4q35 in a specimen.

2 Claims, 17 Drawing Sheets

METHOD FOR DETECTING ORAL SQUAMOUS-CELL CARCINOMA

TECHNICAL FIELD

The present invention relates to a method for detecting cancer, which comprises detecting gene alterations that exist in the specific chromosomal region of a specimen.

BACKGROUND ART

Oral squamous-cell carcinoma (OSCC) is classified as a head and neck cancer and is a tumor that is mainly generated from oral mucous membrane epithelia and the like. Among head and neck cancers, OSCC incidence is as high as about 35% and has some influences on 270,000 people worldwide every year (Parkin, D. M., et al., CA Cancer J Clin. 55, 74-108, 2002). The most common site of the origin of oral squamous-cell carcinoma is tongue, and the second most common site thereof is gingiva (gum). Oral squamous-cell carcinoma is known to be developed at other mucous membranes of the oral cavity, such as buccal mucosa, palate, and mouth floor. Furthermore, oral squamous-cell carcinoma is also known to be developed at jaw bone or salivary gland.

In recent years, although procedures for diagnosis and treatment for oral squamous-cell carcinoma have been advanced, the prognosis thereof has remained unimproved. Accordingly, it has been desired to discover a causative gene for oral squamous-cell carcinoma and to elucidate the functions for establishment of new strategic understandings for effective therapeutic methods and chemical prevention.

It has been known from long ago that the onset of cancer is caused by mutation in the proteins of cells or a quantitative change thereof. The recent development of genetic engineering has enabled amplification of genes encoding specific proteins and the analyses of gene mutations in cancer cells, and it has brought on significant progression in the field of cancer researches. To date, the analysis and identification of what are called "oncogene" associated with malignant transformation of cells or abnormal proliferation of cancer cells have been proceeded. On the other hand, antioncogenes, whose mutation or decrease in expression would lead to malignant transformation, have come under the spotlight in recent years. As such antioncogenes, an Rb gene of retinoblastoma, a p53 gene and an APC gene of colon cancer, a WT1 gene of Wilms' tumor, and so on have been discovered so far. A case of a cancer-suppressing agent that utilizes the WT1 gene has also been reported (WO2003/002142).

Moreover, it has been gradually revealed that the abnormity of, not only a single gene, but also multiple genes, is involved in the onset, malignant transformation and metastasis of cancer, etc. It has been considered that there would be more unidentified oncogenes and antioncogenes. A large number of genes having an effect of suppressing cancer have been known. In order to select such antioncogenes, an approach for finding such genes by staining chromosomal DNA to visualize the gene mutation of a patient (Yasuhide Yamashita, et al., World J Gastroenterol, 11(33): 5129-5135, 2005) and a method comprising roughly selecting a gene deletion by an LOH (Loss of Heterozygosity) analysis and narrowing down an important gene region (WO01/032859) have been applied in many cases. However, these methods have been disadvantageous in that a DNA deletion region to be detected would be large and in that large amounts of time and labor would be required for an operation to narrow down an important gene region. Thus, these methods have had certain limits as means for finding out antioncogenes. Furthermore, it has been difficult to determine the degree of malignancy by conventional methods for separating and differentiating the pathologic condition of cancer.

In order to solve the aforementioned problems, the present inventors have discovered novel antioncogenes such as a CDKN2A gene, a CDH1 gene, an MGMT gene, an RARB gene, an RASSF1A gene, a DAPK gene, an MLH1 gene and an LRP1B gene, and they have reported such genes (Nakagawa T, Pimkhaokham A, Suzuki E, Omura K, Inazawa J, Imoto I., Genetic or epigenetic silencing of low density lipoprotein receptor-related protein 1B expression in oral squamous cell carcinoma. Cancer Sci 2006; 97: 1070-4). Further, it has also been reported that an FAT gene functions as an antioncogene and that the homozygous deletion of the FAT gene may cause the tumorigenic transformation of oral cavity cancer (Nakaya K, Yamagata H. D., Arita N, et al., Identification of homozygous deletions of tumor suppressor gene FAT in oral cancer using CGH-array. Oncogene 2007; 26: 5300-8). However, in order to analyze the mechanism of a cause of cancer at a genetic level and utilize it in diagnoses, it has been necessary to analyze more gene mutations.

DISCLOSURE OF THE INVENTION

Successful elucidation of the mechanism of malignant transformation of oral-cavity-derived cells and mainly oral-epithelium-derived cells at the gene level will enable detection of malignant transformation of oral-cavity-derived cells at the gene level, diagnosis of the malignancy of oral squamous-cell carcinoma, and suppression of the advancement thereof. Furthermore, it will also enable establishment of methods for selecting and developing drugs, as well as therapeutic methods based on such mechanisms. Specifically, this object can be achieved by identifying genes exhibiting characteristic behavior in oral squamous-cell carcinoma cases and then carrying out technical examination mainly targeting such genes. Hence, it is an object to be achieved by the present invention to provide a method for detecting cancer and a cell growth inhibiting agent by the identification of genes exhibiting characteristic behavior in cancers such as oral squamous-cell carcinoma.

Comparative Genomic Hybridization (CGH) is the best method for conveniently and rapidly analyzing genetic abnormalities accompanying amplification or deletion of numerous genes in the genome or inactivation of genes. To analyze genetic abnormalities in the genome involved in malignant transformation and higher cancer malignancy, the present inventors have selected 800 types or 4500 types of BAC/PAC DNA to be subjected to CGH assay (MCG CancerArray-800, MCG Whole Genome-4500; Takada H., et al., Cancer Sci. 96, 100-105, 2005, Inazawa J., et al., Cancer Sci. 95, 559-563, 2004). As a result, the present inventors have screened for a gene deleted with high frequency in cancer. Further, the inventors have combined a COBRA (combined bisulfite restriction analysis) method (Xiong Z and Laird P. W., Nucleic Acids Res 25: 2532-2534. 1997) with an RT-PCR method, and they have succeeded in identification of a cancer-associated gene that promotes malignant transformation of oral-cavity-derived cells; that is, a Melatonin Receptor 1A (MTNR1A) gene. Moreover, the present inventors have succeeded in discovering that deletion or inactivation of the MTNR1A gene, and specifically a decrease in the MTNR1A protein, significantly promotes the proliferation of oral squamous-cell carcinoma. Thus, the present inventors have completed the present invention.

The present invention provides a method for detecting cancer, which comprises detecting at least one gene alteration existing in chromosomal region 4q35 in a specimen.

Preferably, the gene whose alteration is to be detected is at least one selected from MTNR1A, F11, KLKB1, CYP4V2, DKFZP564J, and TRL3.

Preferably, the gene alteration is deletion and/or inactivation of the gene.

Preferably, the gene alteration is inactivation of the gene due to methylation of CpG islands.

Preferably, the gene is MTNR1A.

Preferably, the gene alteration is detected using a DNA chip method, a Southern blot method, a Northern blot method, a real-time RT-PCR method, a FISH method, a CGH method, an array CGH method, a bisulfite sequencing method, or a COBRA method.

The present invention further provides a method for detecting cancer, which comprises detecting the amount of a protein translated from at least one gene selected from MTNR1A, F11, KLKB1, CYP4V2, DKFZP564J, and TRL3.

Preferably, the amount of a protein is detected by an immunohistochemical method.

Preferably, the specimen is a tissue derived from oral cavity.

Preferably, the cancer is oral squamous-cell carcinoma.

Preferably, malignant transformation including the degree of malignancy of the specimen is detected.

The present invention further provides a method for suppressing cell growth, which comprises introducing into cells in vitro at least one gene selected from MTNR1A, F11, KLKB1, CYP4V2, DKFZP564J and TRL3, or a protein encoded by at least one gene selected from MTNR1A, F11, KLKB1, CYP4V2, DKFZP564J and TRL3.

The present invention further provides a cell growth suppressing agent, which comprises at least one gene selected from MTNR1A, F11, KLKB1, CYP4V2, DKFZP564J and TRL3, or a protein encoded by at least one gene selected from MTNR1A, F11, KLKB1, CYP4V2, DKFZP564J and TRL3.

According to the present invention, it has become possible to precisely understand signs of malignant transformation in an oral-cavity-derived cell specimen and the malignancy found in such specimen. Furthermore, proliferation of oral squamous-cell carcinoma can be suppressed by introducing an MTNR1A gene or a transcription product thereof into oral squamous-cell carcinoma.

Figure 1A:
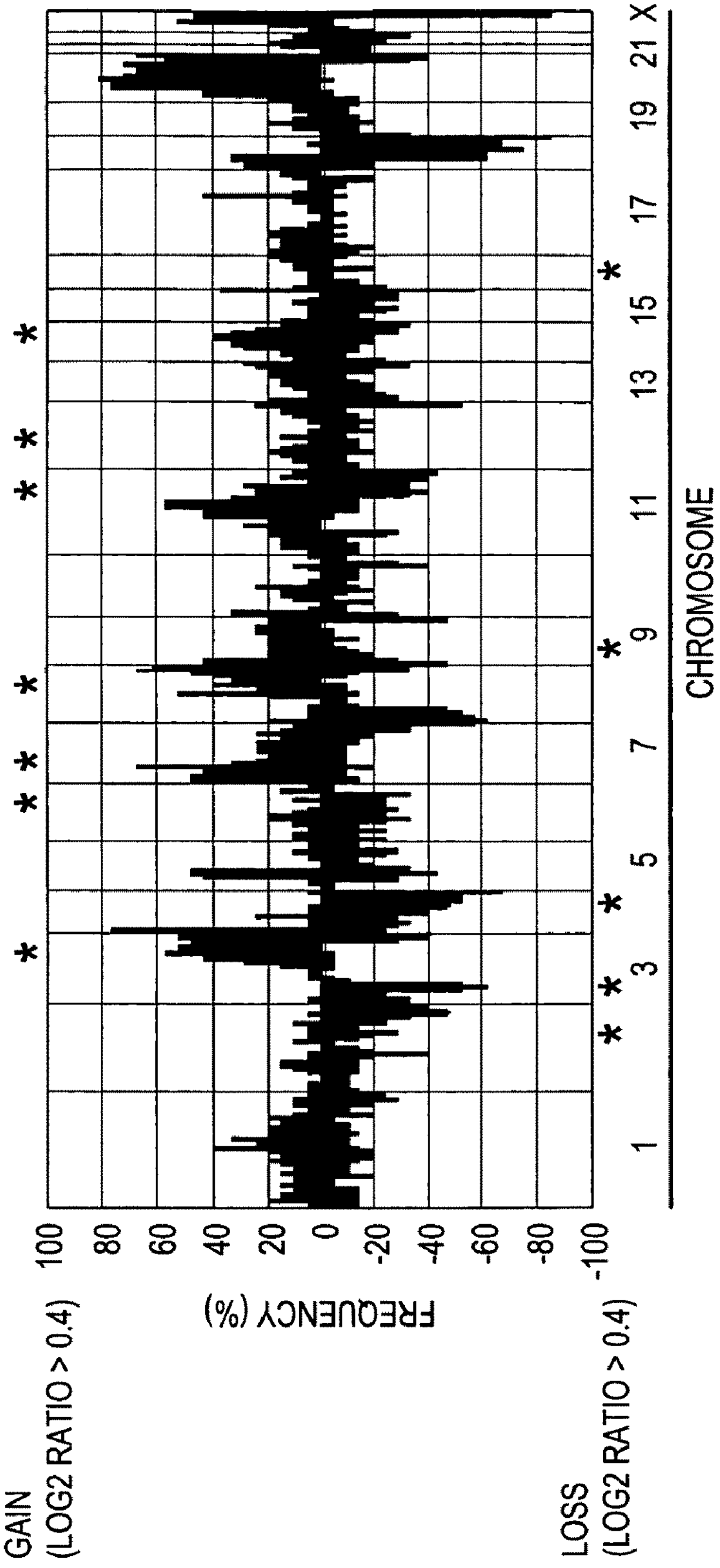
[FIG. 1]

(A) The frequency of amplification and deletion of copy number in the entire genomes of 21 types of oral squamous-cell carcinoma cell lines, which was determined using MCG Cancer Array-800 (amplification: a value of 0 or greater is expressed with green; deletion: a value of 0 or smaller is expressed with red). Clones were aligned in order of chromosomes 1-22, X, and Y based on the UCSC mapping positions (genome.ucsc.edu/) [version May, 2004]. Each asterisk represents a region for which high-level amplification (log 2ratio>−2) or homozygous deletion (log 2ratio<−2) was observed.

(B) Typical images obtained by array CGH analysis (MCG Whole Genome Array-4500) conducted for the TOSCa-52 and SAS cell lines. Significant deletion of RP11-213A19 in 4q35 in the TOSCa-52 cells and significant deletion of RP11-178C12 in the SAS cells are indicated with the red signals (red arrows).

(C) A map that covers a homozygous deletion region of chromosome 4q35 in the TOSCa-24, 36, 52 and 55, and SAS cell lines. A horizontal line represents BAC spotted on the array (in which the red line indicates the BAC of the homozygous deletion region having a Log 2 ratio of smaller than −2). A detailed map of the homozygous deletion-related regions of the 5 cell lines was produced by genomic PCR using STS markers (1: SHGC-8050; 2: RH48688; 3: SHGC-156018; 4: RH45826; 5: SGGC-140659; 6: GDB315917; 7: SHGC-50723; 8: SHGC-140376; and 9: WI-3160). The homozygous deletion regions and remaining regions were expressed with the red ● (filled circle) and the red ○ (open circle). Three independent regions (regions A-C) which are deleted in one or more cell lines were detected in the 5 cell lines. The approximately 1-Mb homozygous deletion regions of the 5 cell lines, which were determined with STS markers, are expressed with horizontal filled red arrows. Genes existing around such regions are indicated with the arrows (homozygous deletion-7 genes indicated with the red arrows; a remaining gene indicated with the black arrow) (the direction indicates a transcription direction).

[FIG. 2]

(A) Genomic PCR analysis of genes existing around the 4q35 homozygous deletion regions of 39 oral squamous-cell carcinoma cell lines. Homozygous deletions of TRL3, DKFZP564J, CYP4V2, KLKB1, F11, MTNR1A, and FAT were detected in two or three squamous cell-carcinoma cell lines. RT-7 is an immortalized cell line from normal oral epithelial cells, and LCL is a lymphoblast cell line.

(B) The mRNA expression analysis by RT-PCR of the TRL3 gene, DKFZP564J gene, CYP4V2 gene, KLKB1 gene, F11 gene, MTNR1A gene and FAT gene in a squamous cell-carcinoma cell line, an RT7 cell line, and primary cells of normal oral cavity mucosa. It is particularly notable that the MTNR1A gene was expressed in the RT7 cells and in the primary cells of normal oral cavity mucosa, whereas a decrease in the expression level of this gene was observed in 33 out of 37 cell lines in which there was no homozygous deletion of the MTNR1A gene.

(C) MTNR1A expression was recovered by a demethylation treatment performed on cells in which the gene was not expressed. The cells were treated using a 1 μM or 5 μM demethylating reagent 5-aza-dCyd for 5 days and/or using a deacetylation inhibitory agent TSA (100 ng/ml) for 12 hours. GAPDH was used as an internal control.

[FIG. 3]

(A) The CpG island of the MTNR1A gene is indicated by the black arrow, and exon 1 is indicated by being enclosed by a box. Further, the results of the bisulfite sequencing are also shown. The CpG site is indicated by the longitudinal bar on the axis. The transcription initiation position is indicated as +1. Fragments to which the promoter assay was applied are indicated by boldface. Regions to which COBRA and the bisulfite sequencing were applied are indicated by thin horizontal lines. The restriction sites of BstUI and TaqI in COBRA are indicated by dashed lines with arrows. There are shown the results of the bisulfite sequence method applied to the CpG site of the MTNR1A gene to an oral epithelial cell line (+) in which the MTNR1A gene is expressed and an oral epithelial cell line (−) in which the MTNR1A gene is not expressed. The symbol □ in the CpG site indicates "not-methylated," and the symbol ■ in the CpG site indicates "methylated." PCR primers used in methylation-specific PCR (MSP) are indicated by the arrows.

(B) There are shown the results of the analysis of the MTNR1A gene CpG island by COBRA, after completion of the restriction treatment of regions 1 and 3 with BstUI and region 2 with TaqI in the oral squamous-cell carcinoma cell line and in RT7. The arrow indicates methylated CpG, and the arrow point indicates not-methylated CpG.

(C) There is shown the promoter activity of the MTNR1A CpG island. An empty vector (pGL3) and a vector comprising three different sequences (nucleotide lengths of fragments 1-4: 118 bp, 190 bp, 257 bp, and 565 bp) in a highly methylated region of MTNR1A were introduced into NA cells and OM2 cells. Luciferase activity was standardized by an internal control.

[FIG. 4]

The methylation status of CpG island and the expression level of the MTNR1A gene in primary clinical specimens of oral squamous-cell carcinoma.

(A) There are shown the results of MSP analysis of the MTNR1A promoter region of each primary specimen of oral squamous-cell carcinoma. Using a methylation-specific primer (M) and an unmethylation-specific primer (U), specimens were amplified in parallel by MSP. NA and HSC-5 cell lines were used as controls of methylation or unmethylation.

(B) There are shown the results of the bisulfite sequence method applied to the CpG island of the MTNR1A gene of each primary specimen of oral squamous-cell carcinoma analyzed by MSP. Please refer to the descriptions of FIG. 3*a*. PCR primers used in MSP are indicated by the arrows.

(C) There are shown the results of an immunostaining analysis method applied to the MTNR1A protein. There are shown 2 positive cases in which 10% or more of cancer cells have been stained and 2 negative cases in which less than 10% of cancer cells have been stained. The adjacent normal oral cells are positive.

(D) The Kaplan-Meier curve of the whole survival rate of 50 patients suffering from primary oral squamous-cell carcinoma. Patients who have turned out negative in terms of the expression of the MTNR1A gene in tumor clearly have a poorer prognosis than patients who have turned out positive (P=0.0208).

[FIG. 5]

The effect of the expression recovery of the MTNR1A gene on the growth of OSCC cells.

(A) The results of Western blotting of HSC-7 cells and NA cells, into which an MTNR1A vector (pCMV-3Tag4A-FLAG-MTNR1A) and an empty vector (pCMV-3Tag4A-mock) have been introduced. 10 μg of protein obtained from the cells 24 hours after the transduction was analyzed by the Western blotting method, and thus it was confirmed that an MTNR1A protein was expressed as a result of the transduction.

(B) The culture results obtained 2 weeks after the transduction using the vectors and selection of drug-resistant colonies. The number of large colonies in MTNR1A-introduced cells is clearly smaller than that in empty-vector (mock)-introduced cells (left of B). The results of counting colonies with a size of 2 mm or greater (right of B).

[FIG. 6]

(A) The expression status of a DKFZP564J gene and a CYP4V2 gene in cell lines in which the expression levels of the aforementioned genes had been decreased, which were treated with 5-aza-dCyd and/or TSA.

(B) The methylation status of CpG island around the transcription initiation regions of the DKFZP564J gene and the CYP4V2 gene, which was examined by the COBRA method.

[FIG. 7]

(A and B) The status of methylation and expression of the MTNR1A genes in the cancerous portion and non-cancerous portion of each primary clinical specimen of oral squamous-cell carcinoma.

(C) The results of an immunostaining analysis method applied to an MTNR1A protein.

PREFERRED EMBODIMENT FOR CARRYING OUT THE INVENTION

Hereafter, the present invention will be described more in detail.

(1) Method for Detecting Cancer

The method for detecting cancer according to the present invention is characterized in that it comprises detecting at least one gene alteration existing in chromosomal region 4q35 in a specimen. More preferably, a gene to be detected is an MTNR1A gene.

As a result of the human genome project, transcription products of the MTNR1A gene are already known. The gene is located on chromosomal region 4q35. The protein encoded by the MTNR1A gene is known to be a receptor protein of melatonin that is a pineal hormone. However, the fact that the MTNR1A gene is an important cancer-associated gene involved in the onset of oral squamous-cell carcinoma or the malignancy thereof was unknown before the present invention.

As described above, the detection method of the present invention comprises detecting deletion or inactivation of the MTNR1A gene in oral-cavity-derived cells or oral squamous-cell carcinoma.

Preferred examples of oral-cavity-derived cells or oral squamous-cell carcinoma to be subjected to detection of deletion or inactivation of the MTNR1A gene include biopsied tissue cells of specimen donors.

Such tissue cell specimen may be the oral-cavity-derived cell of a healthy subject or the cancerous tissue of an oral squamous-cell carcinoma patient. In practice, examples of a major target tissue specimen that can be used herein include: a tissue obtained from a lesion in which suspected malignant transformation of the mucous membrane of oral cavity, tongue, gum, or the like is observed by a test or the like; and an oral squamous-cell carcinoma tissue that has been confirmed to be derived from oral squamous-cell carcinoma and thus must be subjected to determination of malignancy or the stage progression of oral squamous-cell carcinoma.

In a case where the deletion or inactivation of the MTNR1A gene is observed in "a tissue obtained from a lesion in which suspected malignant transformation of oral-cavity-derived tissues or cells is observed in a test or the like" by the detection method of the present invention, it is understood that such lesion tissue will reach (or has reached) the state of malignant transformation so that the degree of malignancy of the disease will increase. Thus, there is a demonstrated urgent need for implementation of a full-scale therapy (e.g., elimination of a lesion via a surgery or the like and full-scale chemotherapy). In addition, in a case in which the deletion or inactivation of the MTNR1A gene is observed in "an oral squamous-cell carcinoma tissue that has been confirmed to be derived from oral squamous-cell carcinoma and thus must be subjected to determination of malignancy or the stage progression of oral squamous-cell carcinoma," it is also understood that the degree of malignancy of the cancerous tissue will increase. Thus, there is a demonstrated urgent need for implementation of full-scale therapy (e.g., elimination of a lesion via a surgery or the like and full-scale chemotherapy). An oral squamous-cell carcinoma tissue collected as a specimen may be subjected to necessary treatment such as preparation of DNA or RNA from the collected tissue followed by the detection method of the present invention.

Next, as an example of the present invention, detection of deletion or inactivation of the MTNR1A gene will be explained. It is to be noted that, in the present invention, in addition to alteration of the MTNR1A gene, alteration of genes existing in chromosomal region 4q35 (for example, F11, KLKB1, CYP4V2, DKFZP564J, TRL3, etc.) may also be detected in the same matter as detection of the MTNR1A gene.

(i) Detection of MTNR1A Gene Deletion

Examples of a typical method by which MTNR1A gene deletion can be directly detected include a CGH (Comparative Genomic Hybridization) method and a FISH (Fluorescence in situ hybridization) method. According to the detection method in this embodiment, BAC (Bacterial Artificial Chromosome) DNA, YAC (Yeast Artificial Chromosome) DNA, or PAC (P1-drived Artificial Chromosome) DNA (hereinafter, also referred to as BAC DNA or the like) having the MTNR1A gene is labeled and then FISH is performed, so that the presence or the absence of the MTNR1A gene (that is, MTNR1A gene deletion) can be detected. Specific examples of such BAC DNA having the MTNR1A gene include RP11-213A19 and PR11-178C12.

It is preferable and practical to carry out the method in the above embodiment with the use of a genomic DNA-immobilized matrix. The amount of BAC DNA or the like obtained in a conventional manner is so small that a large number of genomic DNA-immobilized matrices cannot be produced for practical application. Thus, it is necessary to obtain gene amplification products of such DNA. (A gene amplification process for this purpose is referred to as "infinite amplification" in some cases.) Upon infinite amplification, BAC DNA or the like is first digested with a four-base recognition enzyme such as Rsa I, Dpn I, Hae III, or the like, followed by ligation with the addition of an adaptor. An adaptor comprises oligonucleotides having 10 to 30 bases and preferably 15 to 25 bases. Double strands of such adaptor have sequences complementary to each other. After annealing, the 3' end of one of the oligonucleotides, at which a blunt end is formed, must be phosphorylated. Next, a primer having a sequence identical to the other oligonucleotide of the adaptor is used for amplification via PCR (polymerase chain reaction). Thus, infinite amplification can be carried out. Meanwhile, it is also possible to use, as a detection probe, an aminated oligonucleotide comprising 50 to 70 bases, which is inherent to BAC DNA or the like.

BAC DNAs or the like subjected to infinite amplification are immobilized on a matrix and preferably on a solid matrix. Accordingly, a desired DNA-immobilized matrix can be produced. An example of such solid matrix is more preferably a glass plate. Such a solid matrix made of glass or the like is more preferably coated via adhesion with poly-L-lysine, aminosilane, gold, aluminium, or the like.

The concentration of DNA subjected to infinite amplification to be spotted on a matrix is preferably 10 pg/μl to 5 μg/μl and more preferably 1 ng/μl to 200 ng/μl. The amount of the same to be spotted on the matrix is preferably 1 nl to 1 μl and more preferably 10 nl to 100 nl. In addition, the size and the shape of each spot that is immobilized on the matrix are not particularly limited. In terms of size, such spot may have a diameter ranging from 0.01 to 1 mm, for example. In addition, the shape of such spot may be a circle or ellipse from an overhead view. The thickness of a dry spot is not particularly limited; however, it may be 1 to 100 μm. Further, the number of spots is not particularly limited; however, it may be 10 to 50,000 spots and more preferably 100 to 5,000 spots on the matrix used. DNAs are spotted singly to quadruplicate. However, preferably, DNAs are spotted in duplicate or triplicate.

Regarding preparation of dry spots, it is possible to produce dry spots by, for example, spotting BAC DNAs or the like subjected to infinite amplification on a matrix with the use of a spotter, forming a plurality of spots thereon, and drying the spots. Examples of a spotter that can be used include an inkjet printer, a pin-array printer, and a bubble jet (trademark) printer. An inkjet printer is desirably used. For instance, GENESHOT (NGK INSULATORS; Nagoya, Japan) or the like can be used.

As described above, it is possible to produce a desired DNA-immobilized matrix by immobilizing BAC DNAs or the like subjected to infinite amplification onto a matrix, and preferably, onto a solid matrix.

In addition, an example of a means of directly detecting the deletion of the MTNR1A gene is the Southern blot method. The Southern blot method is a method for detecting the presence of the MTNR1A gene in a specimen by separating and immobilizing genomic DNA obtained from the specimen and detecting hybridization of such genomic DNA with the MTNR1A gene.

(ii) Detection of MTNR1A Gene Inactivation

It has been reported that transcriptional inactivation occurs when a CpG-rich promoter and an exon region are densely methylated (Bird A P., et al., Cell, 99, 451-454, 1999). In the cases of cancer cells, CpG islands are frequently and densely methylated, when compared with other regions, and thus hypermethylation of a promoter region is deeply involved in the inactivation of an antioncogene of a cancer (Ehrlich M., et al, Oncogene, 21, 6694-6702, 2002). As described below, CpG islands existing in an exon of the MTNR1A gene was actually found to have promoter activities. In addition, the extent of methylation of the CpG islands strongly correlated with suppression of the expression of the MTNR1A gene in some oral squamous-cell carcinoma cases.

In addition, it was possible to demethylate such CpG islands by culturing such oral squamous-cell carcinoma cells in the presence of 5-azadeoxycytidine (5-aza-dCyd) serving as a demethylating reagent. As a result, it was possible to recover the expression level of the MTNR1A gene. Based on the above results, it has been revealed that hypermethylation of CpG islands is a cause of frequently occurring suppression of the expression of an antioncogene in squamous-cell carcinoma.

Recovery of the MTNR1A gene expression level can be examined using the above detection means, specifically by causing a demethylating reagent (e.g., 5-azadeoxycytidine) to act on a cell specimen (a primary cancer cell derived from a cancerous tissue) that has been revealed to exhibit a decreased MTNR1A gene expression level. More specifically, when the expression level of the MTNR1A gene can be recovered by causing a demethylating reagent to act on a cell specimen, a factor that suppresses the gene in the cell specimen is methylation of CpG islands. Hence, a reasonable anti-tumor effect is expected with the administration of a drug having a demethylating effect to a specimen donor.

(2) Method for Inhibiting Cell Growth and Cell Growth Inhibitor

According to the present invention, there are further provided a method for inhibiting cell growth which comprises introducing at least one gene selected from a MTNR1A, F11, KLKB1, CYP4V2, DKFZP564J, or TRL3 gene or a protein which is an expression product of such a gene into cells in vitro, and a cell growth inhibitor comprising said gene or protein.

For handling at least one gene selected from the MTNR1A, F11, KLKB1, CYP4V2, DKFZP564J or TRL3, cDNAs obtained from cultured cells through publicly known methods to those skilled in the art may be used, or enzymatically synthesized ones through PCR method may be also used. When DNA is obtained through PCR method, PCR is performed using human chromosomal DNA or cDNA library as a template, and primers designed to amplify a nucleotide sequence of interest. DNA fragments amplified through PCR can be cloned in an appropriate vector which can proliferate in a host such as *E. coli.*

Manipulations such as preparation of detection probes or primers for at least one gene selected from the MTNR1A, F11, KLKB1, CYP4V2, DKFZP564J, or TRL3 gene and cloning of target genes are already known to those skilled in the art. For example, such manipulations can be performed according to methods described in Molecular Cloning: A Laboratory Manual, $2^{nd}$ Ed., Cold Spring Harbor Laboratory, Cold Spring Harbor, N.Y., 1989, Current Protocols in Molecular Biology, Supplement 1 to 38, John Wiley & Sons (1987-1997), or the like.

At least one gene selected from MTNR1A, F11, KLKB1, CYP4V2, DKFZP564J, or TRL3 gene can be used in the form of a recombinant vector having such a gene incorporated therein. Examples of the vector to be used herein may include viral vectors and vectors for expression in animal cells. Preferably, viral vectors are used. Examples of such viral vector include retroviral vectors, adenoviral vectors, adeno-associated virus vectors, baculovirus vectors, vaccinia virus vectors, and lentivirus vectors. Of these, retroviral vectors are particularly preferred to use, since retroviral vectors enable stable and long-term expression of a foreign gene that had been incorporated into such vectors, through incorporation of the virus genome into a host chromosome after infection into cells.

Examples of the vector for expression in animal cells to be used herein may include pCXN2 (Gene, 108, 193-200, 1991), PAGE207 (JP Patent Publication (Kokai) No. 6-46841 (1994)) or variants thereof.

The above recombinant vector can be produced through transfection into an appropriate host to effect transformation, followed by culturing of thus obtained transformant. When the recombinant vector is a viral vector, animal cells capable of producing viruses are used as the host to be transfected with such a viral vector. For example, COS-7 cells, CHO cells, BALB/3T3 cells, and HeLa cells are use. Examples of the host to be used for retroviral vectors include ψCRE, ψCRIP, and MLV. Examples of the hosts to be used for adenoviral vectors or adeno-associated virus vectors include human embryonic kidney-derived 293 cells. Viral vectors can be transfected into animal cells by a calcium phosphate method. Moreover, when the recombinant vector is a vector for expression in animal cells, the *E. coli* K12 strain, the HB101 strain, and the DH5α strain, or the like can be used as the host to be transfected with such a vector. Transformation of *E. coli* is publicly known to those skilled in the art.

Thus obtained transformant is cultured in an appropriate medium under appropriate culture conditions, respectively. For example, a transformant of *E. coli* can be cultured using a liquid medium at a pH of about 5 to 8 containing carbon sources, nitrogen sources, inorganic substances, and the like which are essential for growth. The culture is normally carried out at 15° C. to 43° C. for about 8 to 24 hours. In this case, the recombinant vector of interest can be obtained through usual DNA isolation and purification methods, on completion of culture.

Moreover, transformants of animal cells can be cultured using a medium such as a 199 medium, an MEM medium, or a DMEM medium containing about 5% to 20% fetal bovine serum. The pH of the medium is preferably about 6 to 8. The culture is normally carried out at 30° C. to 40° C. for about 18 to 60 hours. In this case, since virus particles containing a target recombinant vector are released into a culture supernatant, the recombinant vector can be obtained through concentration and purification of the virus particles by a cesium chloride centrifugation method, a polyethylene glycol precipitation method, a concentration method using a filter, or the like.

The cell growth inhibitor of the present invention can be produced by mixing the abovementioned gene serving as an active ingredient with a base that is commonly used for gene therapeutic agents. Moreover, when such a gene is incorporated into a viral vector, virus particles containing the recombinant vector are prepared, and are then mixed with a base that is commonly used for gene therapeutic agents.

As to the base to be used for mixing the abovementioned gene or protein serving as an active ingredient, bases commonly used for injectable agents can be used. Examples thereof include: distilled water: salt solutions containing sodium chloride, a mixture of sodium chloride and mineral salts, or the like: solutions of mannitol, lactose, dextran, glucose, or the like: amino acid solutions of glycine, arginine, or the like: and mixed solutions having glucose solution with an organic acid or salt solution. Alternatively, these bases can also be prepared into injectable agents in the form of a solution, suspension, or dispersion, with use of auxiliary agents such as an osmoregulator, a pH adjuster, a vegetable oil, and a surfactant, in accordance with usual methods which are already known to those skilled in the art. These injectable agents can also be prepared in the form of a pharmaceutical preparation to be dissolved at the time of use, through operations such as powderization or lyophilization.

The form of administration of the cell growth inhibitor of the present invention may be either systemic administration such as usual intravenous administration and intraarterial administration, or local administration such as local injection and oral administration. Furthermore, administration of the cell growth inhibitor may also take a combined form with catheterization, gene introduction technology, or surgical operation.

The administration dose of the cell growth inhibitor of the present invention varies depending on the age and gender of the patient, the symptom, the administration route, the frequency of administration, and the dosage form. Generally, the daily dose for an adult is within a range of about 1 μg/kg of body weight to 1000 mg/kg of body weight, and preferably a range of about 10 μg/kg of body weight to 100 mg/kg of body weight, in terms of weight of recombinant gene. The frequency of administration is not particularly limited.

The present invention is hereafter described in greater detail with reference to the following examples, although the technical scope of the present invention is not limited thereto.

EXAMPLES

Example 1

Gene Alteration in Oral Squamous-Cell Carcinoma

Figure 1C:
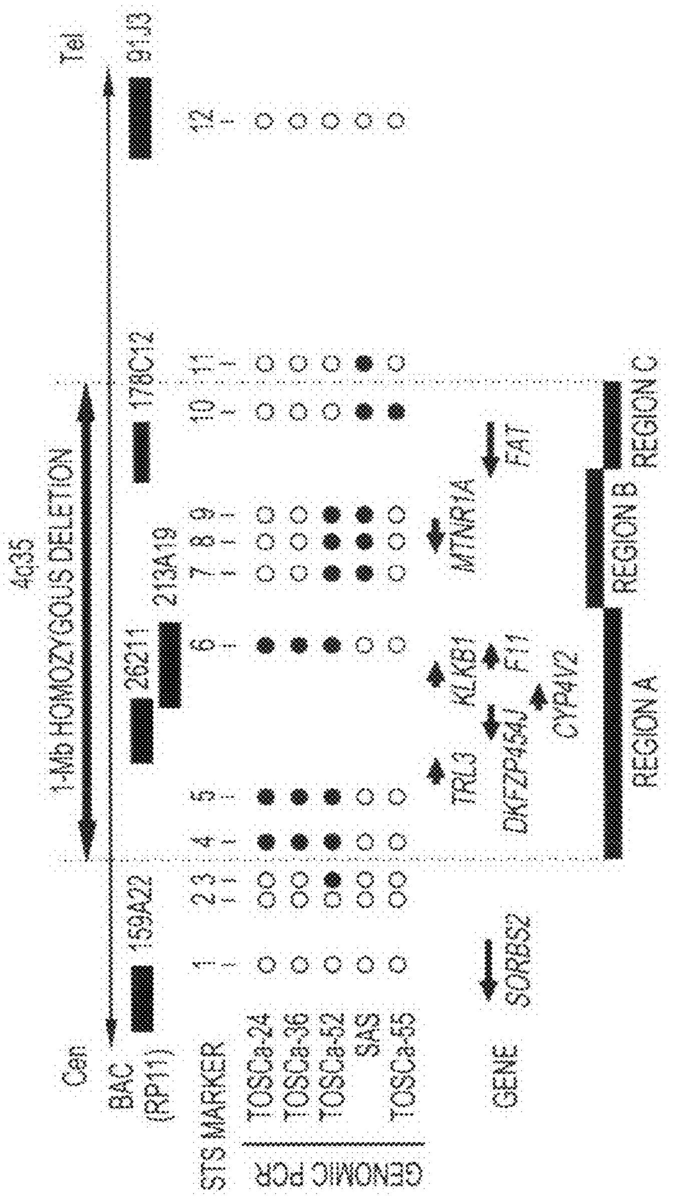
Figure 1B:
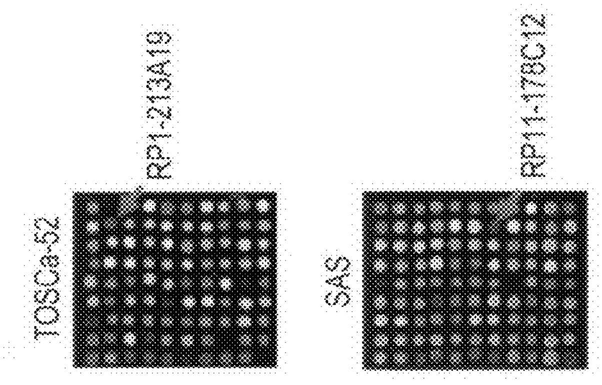

In order to detect a novel gene alteration in oral squamous-cell carcinoma, CGH array analysis was made using genomic DNAs prepared from 21 types of oral squamous-cell carcinoma cell lines obtained by eliminating the initial 18 types of cell lines from 25 types of oral squamous-cell carcinoma cell lines (OM-1, OM-2, TSU, ZA, NA, Ca9-22, HOC-313, HOC-815, HSC-2, HSC-3, HSC-4, HSC-5, HSC-6, HSC-7, KON, SKN-3, HO-1-N-1, KOSC-2, Sa3, SAS, KOSC-3, HO-1-u-1, T3M1C12, T3M1CI-10, and HSQ89) and from 14 types of oral squamous-cell carcinoma cell lines (Tosca-2S, 7, 18, 23, 24, 30, 32, 36, 45, 50, 52, 55, 58S1, and 65), and employing MGC Cancer Array-800, and MGC Whole Genome Array-4500. In addition, a genome extracted from the cell line (RT7) derived from normal oral epithelium was labeled with Cy5 as a control. Genomic DNAs prepared from the above oral squamous-cell carcinoma cell lines were used as test DNAs and labeled with Cy3. Specifically, each genomic DNA (0.5 μg) digested with Dpn II was labeled using a BioPrime Array CGH Genomic Labeling System (Invitrogen) in the presence of 0.6 mM dATP, 0.6 mM dTTP, 0.6 mM dGTP, 0.3 mM dCTP, 0.3 mM Cy3-dCTP (oral squamous-cell carcinoma cells), or 0.3 mM Cy5-dCTP (normal cells). Cy3- and Cy5-labeled dCTPs were obtained from GE Healthcare. Ethanol was added so that the genomic DNA labeled with Cy3 or Cy5 was precipitated in the presence of Cot-1 DNA (Invitrogen). The resultant was dissolved in 120 μl of a hybridization mixture (50% formamide, 10% Dextran sulfate, 2×SSC (1×SSC: 150 mM NaCl/15 mM Sodium Citrate), 4% sodium dodecyl sulfate, pH 7.0). After 30 minutes of incubation at 37° C., the resultant was introduced onto a CGH array set in a hybridization machine (GeneTAC; Harvard Bioscience), followed by 48 to 72 hours of hybridization. Subsequently, the CGH array was washed in a 50% formamide/2×SSC (pH 7.0) solution at 50° C. for 15 minutes and then washed at 50° C. for 15 minutes in 2×SSC/0.1% SDS. After air-drying, the CGH array was monitored for fluorescence derived from Cy3 and Cy5 using GenePix 4000B scanner (Axon Instruments, CA, U.S.A.). The thus obtained results were analyzed using a GenePix Pro 6.0 imaging software (Axon Instruments, CA, U.S.A.). The average fluorescence intensity derived from Cy3 was adjusted to be the same as that of fluorescence intensity derived from Cy5, thereby allowing the ratio of Cy3 to Cy5 to be found. When a genome has no abnormality, the resulting ratio becomes 1:1 (log 2 ratio=0). Determination was performed as follows. A ratio of 1.32 (or higher):1 (log 2 ratio=0.4 or more) indicates the presence of genome amplification and a ratio of 4 (or higher):1 (log 2 ratio=2.0 or more) indicates the confirmation of significant amplification. A ratio of 0.75 (or lower):1 (log 2 ratio=−0.4 or less) indicates possible heterozygote deletion in the genome and a ratio of 0.25 (or lower):1 (log 2 ratio=−2 or less) indicates an extremely high possibility of homozygote deletion in the genome. The results are shown in FIGS. 1*a* and 1*b* and Tables 1 and 2.

TABLE 1

High-level amplifications (log2ratio > 2.0) detected in OSCC cell lines by CGH-array analysis using MCG Cancer Array-800 and Whole Genome Array-4500

| | | Locus[a] | | Cell line (Total 21) | | | Number |
|---|---|---|---|---|---|---|---|
| Locus no. | BAC | Chromomal band | Position | n | Name | Possible target gene[b] | of known gene[b] |
| 1 | RP11-201D16 | 3q28-29 | chr3: 193,773,254-193,974,704 | 1 | TOSCa-58S1 | FGF12 | 1 |
| 2 | RP11-81B13 | 6q15 | chr6: 88,549,158-88,724,237 | 1 | TOSCa-2S | None | 16 |
| | RP11-52B15 | 6q15 | chr6: 89,876,894-89,877,257 | 1 | TOSCa-2S | | |
| 3 | RP11-88H8 | 6q16.3 | chr6: 102,875,956-103,063,942 | 1 | TOSCa-2S | None | 0 |
| 4 | RP11-59D10 | 6q22.31 | chr6: 120,850,056-121,030,474 | 1 | TOSCa-55 | None | 9 |
| | RP11-311B1 | 6q22.31 | chr6: 122,660,488-122,751,648 | 1 | TOSCa-55 | | |
| | RP11-374A22 | 6q22.31 | chr6: 124,066,898-124,228,515 | 1 | TOSCa-55 | | |
| 5 | RP11-11D14 | 7p12.3 | chr7: 47,568,937-47,569,205 | 1 | TOSCa-32 | None | 6 |
| 6 | RP11-90N11 | 7p11.2 | chr7: 53,898,011-54,057,902 | 1 | TOSCa-2S | EGFR | 9 |
| | RP11-14K11 | 7p11.2 | chr7: 54,954,314-54,954,933 | 3 | TOSCa-2S, 32, 50 | | |
| | RP11-339F13 | 7p11.2 | chr7: 55,222,879-55,348,131 | 3 | TOSCa-2S, 32, 50 | | |
| | RP11-97P11 | 7p11.2 | chr7: 55,431,590-55,575,284 | 3 | TOSCa-2S, 32, 50 | | |
| | RP11-34J24 | 7p11.2 | chr7: 55,596,472-55,596,912 | 3 | TOSCa-2S, 32, 50 | | |
| | RP11-80L24 | 7p11.2 | chr7: 55,843,666-55,977,803 | 3 | TOSCa-2S, 32, 50 | | |
| 7 | RP11-89K10 | 8q24.21 | chr8: 127,636,702-127,799,435 | 1 | TOSCa-45 | MYC | 2 |
| | RP1-80K22 | 8q24.21 | chr8: 128,735,610-128884782 | 1 | TOSCa-45 | | |
| | RP11-237F24 | 8q24.21 | chr8: 128,817,498-128,822,855 | 1 | TOSCa-45 | | |
| 8 | RP11-35F11 | 11q12.3 | chr11: 62,933,912-63,103,603 | 1 | TOSCa-65 | CCND1, FGF3, FGF4 | 185 |
| | RP11-80B24 | 11q13.1 | chr11: 63,230,447-63,411,884 | 1 | TOSCa-65 | | |
| | RP11-804L21 | 11q13.3 | chr11: 69,333,918-69,343,129 | 4 | TOSCa-2S, 45, 55, 65 | | |
| 9 | RP11-258C1 | 11q22.1 | chr11: 99,810,209-99,988,933 | 1 | TOSCa-55 | BIRC2, BIRC3, YAP1 | 29 |
| | RP11-40B14 | 11q22.1 | chr11: 99,932,373-100,132,253 | 1 | TOSCa-55 | | |
| | RP11-681O17 | 11q22.1 | chr11: 100,365,386-100,536,934 | 1 | TOSCa-55 | | |
| | RP11-750P5 | 11q22.2 | chr11: 101,623,735-102,191,046 | 1 | TOSCa-55 | | |
| | RP11-28I24 | 11q22.2 | chr11: 101,722,105-101,886,737 | 1 | TOSCa-55 | | |
| | RP11-315O6 | 11q22.2 | chr11: 101,724,723-101,939,121 | 1 | TOSCa-55 | | |
| | RP11-817J15 | 11q22.2 | chr11: 101,922,842-102,095,829 | 1 | TOSCa-55 | | |
| | RP11-750P5 | 11q22.2 | chr11: 102,010,717-102,191,009 | 1 | TOSCa-55 | | |
| | RP11-88H18 | 11q22.2-22.3 | chr11: 102,253,679-102,424,014 | 1 | TOSCa-55 | | |
| | RP11-33F6 | 11q22.3 | chr11: 102,496,919-102,497,333 | 1 | TOSCa-55 | | |
| | RP11-2I22 | 11q22.3 | chr11: 102,613,696-102,771,594 | 1 | TOSCa-55 | | |
| | RP11-51M23 | 11q22.3 | chr11: 104,480,486-104,480,901 | 1 | TOSCa-55 | | |
| 10 | RP11-319E16 | 12p13.32-13.31 | chr12: 5,163,936-5,344,301 | 1 | SAS | KRAS2 | 230 |
| | RP11-451H11 | 12p13.31 | chr12: 5,771,103-5,927,033 | 1 | SAS | | |
| | RP11-166G2 | 12p13.31 | chr12: 5,782,525-5,783,146 | 1 | SAS | | |
| | RP11-96K24 | 12p13.1 | chr12: 13,644,252-13,809,265 | 1 | SAS | | |
| | RP11-295I5 | 12p12.1 | chr12: 25,121,736-25,317,791 | 1 | SAS | | |
| | RP11-64J22 | 12p12.1 | chr12: 25,882,999-25,883,554 | 1 | SAS | | |
| | RP11-877E17 | 12p12.1 | chr12: 25,986,021-26,163,998 | 1 | SAS | | |
| | RP11-283G6 | 12p12.1-11.23 | chr12: 26,122,383-26,326,610 | 1 | SAS | | |

TABLE 1-continued

High-level amplifications (log2ratio > 2.0) detected in OSCC cell lines by CGH-array analysis using MCG Cancer Array-800 and Whole Genome Array-4500

| | | Locus[a] | | Cell line (Total 21) | | | Number |
|---|---|---|---|---|---|---|---|
| Locus no. | BAC | Chromomal band | Position | n | Name | Possible target gene[b] | of known gene[b] |
| | RP11-53C3 | 12p12.1 | chr12: 26,255,248-26,255,675 | 1 | SAS | | |
| | RP11-666F17 | 12p11.23 | chr12: 26,671,081-26,857,010 | 1 | SAS | | |
| | RP11-89L4 | 12p11.23 | chr12: 26,832,206-26,832,866 | 1 | SAS | | |
| | RP11-73I12 | 12p11.21 | chr12: 31,300,995-31,457,338 | 1 | SAS | | |
| | RP11-517B23 | 12p11.21 | chr12: 31,362,925-31,533,973 | 1 | SAS | | |
| 11 | RP11-837P6 | 12q21.33-22 | chr12: 91,147,160-91,214,336 | 1 | TOSCa-2S | None | 3 |
| 12 | RP11-205M16 | 12q24.32 | chr12: 125,875,266-126,030,621 | 1 | TOSCa-2S | None | 0 |
| 13 | RP11-2L22 | 14q23.1 | chr14: 58,681,521-58,851,787 | 1 | TOSCa-58S1 | HIF1A | 60 |
| | RP11-79M1 | 14q23.1 | chr14: 59,822,513-59,822,977 | 1 | TOSCa-58S1 | | |
| | RP11-193F5 | 14q23.1 | chr14: 60,271,223-60,505,149 | 1 | TOSCa-58S1 | | |
| | RP11-471N20 | 14q23.1 | chr14: 60,286,133-60,457,690 | 1 | TOSCa-58S1 | | |
| | RP11-64I19 | 14q23.1 | chr14: 60,680,813-60,681,315 | 1 | TOSCa-58S1 | | |
| | RP11-88L10 | 14q23.1 | chr14: 60,704,698-60,870,460 | 1 | TOSCa-58S1 | | |
| | RP11-436G5 | 14q23.1 | chr14: 61,022,970-61,237,453 | 1 | TOSCa-58S1 | | |
| | RP11-79I3 | 14q23.1 | chr14: 61,309,602-61,449,452 | 1 | TOSCa-58S1 | | |
| | RP11-145O12 | 14q23.2 | chr14: 62,681,383-62,848,934 | 1 | TOSCa-58S1 | | |
| | RP11-445J13 | 14q23.2 | chr14: 62,884,544-63,060,428 | 1 | TOSCa-58S1 | | |
| | RP11-14C21 | 14q23.2 | chr14: 63,712,417-63,865,860 | 1 | TOSCa-58S1 | | |
| | RP11-712C19 | 14q23.2 | chr14: 63,767,389-63,819,456 | 1 | TOSCa-58S1 | | |
| | RP11-44K16 | 14q23.2-23.3 | chr14: 63,974,866-64,135,774 | 1 | TOSCa-58S1 | | |
| | RP11-63G22 | 14q23.3 | chr14: 64,463,311-64,463,893 | 1 | TOSCa-58S1 | | |
| | RP11-840I19 | 14q23.3 | chr14: 64,611,598-64,638,980 | 1 | TOSCa-58S1 | | |
| | RP11-305I24 | 14q23.3 | chr14: 66,806,287-67,002,089 | 1 | TOSCa-58S1 | | |
| | RP11-156E22 | 14q23.3 | chr14: 66,847,838-67,014,199 | 1 | TOSCa-58S1 | | |
| | RP11-79B13 | 14q24.1 | chr14: 67,744,258-67,904,880 | 1 | TOSCa-58S1 | | |
| | RP11-108B17 | 14q24.1 | chr14: 67,980,187-68,130,021 | 1 | TOSCa-58S1 | | |

[a]Based on UCSC Genome Browser, March 2006 Assembly.
[b]Genes located around BAC, whose homozygous deletion was validated by genomic PCR and/or FISH.

TABLE 2

Homozygous deletions (log2 ratio < −2.0) detected in OSCC cell lines by array-CGH using MCG Cancer Array-800 and Whole Genome Array-4500

| | | Locus[a] | | Cell line (Total 21) | | | Number |
|---|---|---|---|---|---|---|---|
| Locus no. | BAC | Chromomal band | Position | n | Name | Possible target gene[b] | of known gene[b] |
| 1 | RP11-91A11 | 2q21.2 | chr2: 133,466,940-133,622,645 | 1 | TOSCa-7 | None | 1 |
| 2 | RP11-29N17 | 2q22.1 | chr2: 141,492,118-141,492,588 | 3 | TOSCa-45, T3M1 Clone2, T3M1 CL-10 | LRP1B | 1 |
| 3 | RP11-94D19 | 3p14.2 | chr3: 60,756,984-60,927,060 | 2 | TOSCa-32, 50 | FHIT | 1 |
| 4 | RP11-262I1 | 4q35.1-35.2 | chr4: 187,244,507-187,380,943 | 3 | TOSCa-24, 36, 52 | FAT | 7 |
| | RP11-213A19 | 4q35.2 | chr4: 187,358,363-187,519,645 | 3 | TOSCa-24, 36, 52 | | |
| | RP11-178C12 | 4q35.2 | chr4: 187,742,000-187,910,017 | 2 | TOSCa-55, SAS | | |
| | RP11-182A9 | 4q35.2 | chr4: 187,810,108-187,977,806 | 1 | TOSCa-55 | | |
| 5 | RP11-176P17 | 9p23 | chr9: 9,504,447-9,653,533 | 4 | TOSCa-24, 30, 36, HO-1-u-1, KOSC-3 | PTPRD | 1 |
| | RP11-91E3 | 9p23 | chr9: 9,554,544-9,689,968 | 2 | TOSCa-24,HO-1-u-1, KOSC-3 | | |
| | RP11-6H18 | 9p23 | chr9: 9,722,988-9,862,247 | 2 | TOSCa-24, HO-1-u-1, KOSC-3 | | |
| | RP11-19G1 | 9p23 | chr9: 9,932,058-10,130,641 | 2 | HO-1-u-1, KOSC-3 | | |
| 6 | RP11-113D19 | 9p21.3 | chr9: 20,996,404-21,158,458 | 1 | HSQ89 | CDKN2A, CDKN2B, MTAP | 4 |
| | RP11-344A7 | 9p21.3 | chr9: 21,506,374-21,676,219 | 1 | HSQ89 | | |
| | RP11-145E5 | 9p21.3 | chr9: 21,998,414-22,155,946 | 2 | TOSCa-58S1, HSQ89 | | |
| | RP11-408N14 | 9p21.3 | chr9: 22,155,847-22,309,629 | 1 | TOSCa-58S1, HSQ89 | | |
| | RP11-441I5 | 9p21.3 | chr9: 22,309,530-22,479,595 | 1 | TOSCa-58S1, HSQ89 | | |
| | RP11-11J1 | 9p21.3 | chr9: 22,479,496-22,579,721 | 1 | TOSCa-58S1, HSQ89 | | |
| | RP11-782K2 | 9p21.3 | chr9: 22,584,981-22,585,358 | 1 | TOSCa-58S1, HSQ89 | | |
| | RP11-33O15 | 9p21.3 | chr9: 22,823,087-22,823,490 | 1 | TOSCa-58S1, HSQ89 | | |
| 7 | RP11-61L1 | 16q23 | chr16: 77344719-77345302 | 2 | TOSCa-32, 50 | WWOX | 1 |

[a]Based on UCSC Genome Browser, March 2006 Assembly.
[b]Genes located around BAC, whose homozygous deletion was validated by genomic PCR and/or FISH.

High-level gene amplification could be confirmed for 8 out of the 21 types of oral squamous-cell carcinoma, and it was confirmed in 13 gene loci. Moreover, gene deletion could be confirmed for 16 out of the 21 types of oral squamous-cell carcinoma, and it was confirmed in 7 gene loci.

Example 2

Isolation of Gene Contained in Deletion Region of Chromosome 4q35 of Oral Squamous-Cell Carcinoma In order to determine the range of a homozygous deletion region in oral squamous-cell carcinoma cells (TOSCa-24, 36, 52, 55, and SAS), in which homozygous deletion of chromosomal region 4q35 had been confirmed with the use of array CGH, a series of STS markers (1: SHGC-8050; 2: RH48688; 3: SHGC-156018; 4: RH45826; 5: SGGC-140659; 6: GDB-315917; 7: SHGC-50723; 8: SHGC-140376; and 9: WI-3160) were used to conduct genomic PCR. As a result, it was found that there are 3 homozygous deletion regions in a region of approximately 1 Mb (FIG. 1*c*).

Moreover, from the results of the CGH array and human genome database (genome.uc/sc/edu/), it was confirmed that there are 7 genes (TRL3, DKFZP564J gene, KLKB1 gene, CYP4V2 gene, F11 gene, MTNR1A gene, and FAT gene) in this region.

Figure 2A:
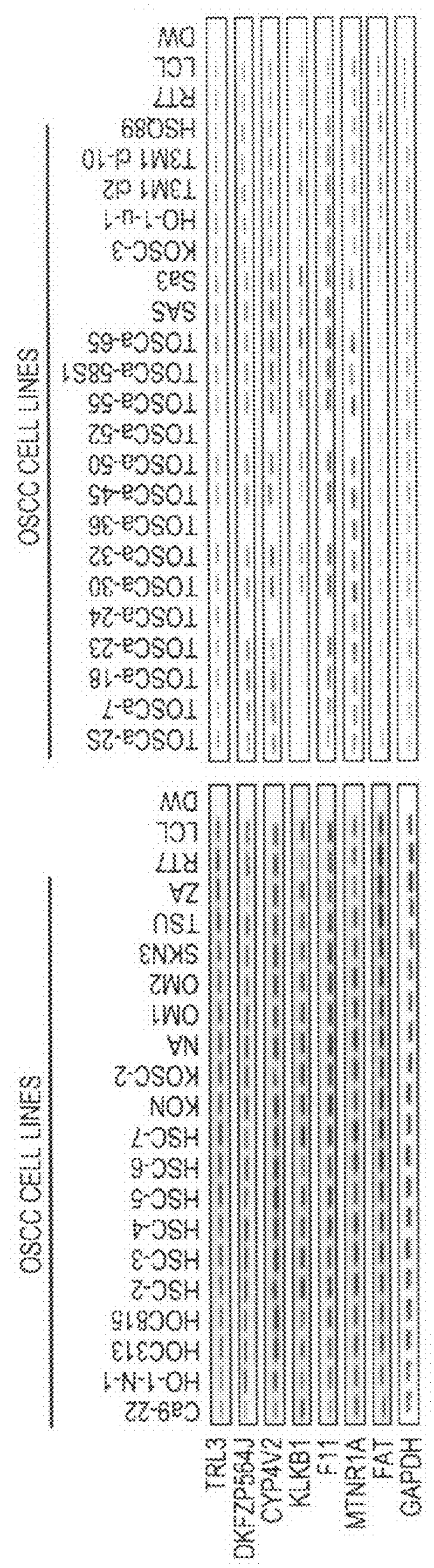

Furthermore, in order to confirm that these genes are homozygously deleted, the aforementioned 39 types of cell lines were subjected to genomic PCR using the primer sets as shown in Supplemental Table 1. As a result, it was found that TRL3 is deleted in two cell lines, DKFZP564J is deleted in three cell lines, CYP4V2 is deleted in three cell lines, KLKB1 is deleted in three cell lines, F11 is deleted in three cell lines, MTNR1A is deleted in two cell lines, and FAT is deleted in two cell lines (FIG. 2*a*).

Example 3

Disappearance of MTNR1A mRNA Expression in Oral Squamous-Cell Carcinoma Cell Lines In order to determine the expression level of the mRNA of the aforementioned 7 types of genes (the TRL3 gene, the DKFZP564J gene, the KLKB1 gene, the CYP4V2 gene, the F11 gene, the MTNR1A gene, and the FAT gene) in each of the aforementioned 39 cell lines, an immortalized cell line RT7 of normal oral epithelial cells, and the primary-cultured epithelial cells from normal oral cavity mucosa, reverse transcriptase (RT)-PCR was carried out.

Specifically, single-stranded cDNA was synthesized from the RNA extracted from each cultured cell line using the SuperScript First-Strand Synthesis System (Invitrogen). PCR was then performed using primer sequences (SEQ ID NOS: 1-44) listed in Table 3. Moreover, a glyceraldehyde-3-phosphate dehydrogenase (GAPDH) gene was used as a control.

TABLE 3

Primer sequences used in this study

| Method | Target | | Forward primer (SEQ ID NO) | Reverse primer (SEQ ID NO) |
|---|---|---|---|---|
| Genomic PCR | TRL3 | | 5'-GCAGCATATATAATTCATG (1) | 5'-TGATGCTGTTAACAATTGCT (2) |
| | DKFZP564J | | 5'-TCACAATATGTGCCTAAATC (3) | 5'-CACAGATAAATATAACACTT (4) |
| | CYP4V2 | | 5'-TCCAGGAGAAAGATGTTAACAC (5) | 5'-CAGATGATATCTAAGGCAC (6) |
| | KLKB1 | | 5'-GTGGTCCCTTAGTTTGCAAAC (7) | 5'-ACTGCATCTGAGCTTTTCCATC (8) |
| | F11 | | 5'-CATCTGGTAGGCATCACGAG (9) | 5'-CTGGGAACCCATTCACACTG (10) |
| | MTNR1A | | 5'-GAAACATCTTTGTGGTG (11) | 5'-ACTGACTTGGCAGTGCAGATA (12) |
| | FAT | | 5'-TAGAGAAGTGAAGGATCACTAC (13) | 5'-GGTGGGTGAGAATAACGGTC (14) |
| RT-PCR | TRL3 | | 5'-AATCCCTTTGTCAAGCAGAAG (15) | 5'-TTGATAATAGAAGCTCTTGGAG (16) |
| | DKFZP564J | | 5'-ATGAGAAGGAGGACAAAGCA (17) | 5'-GCTCCGTGACGTTTGAACCA (18) |
| | CYP4V2 | | 5'-ATACAACTGCAGCTGCAATA (19) | 5'-GGTCTCCTTAATAACACATTC (20) |
| | KLKB1 | | 5'-ATGGGGCTTCTCGAAGGAG (21) | 5'-CAGCACAGACCATCCGTTG (22) |
| | F11 | | 5'-CCAGAAGAGATACAGAGGACA (23) | 5'-CTCGTGATGCCTACCAGATG (24) |
| | MTNR1A | | 5'-GGTGTATCGGAACAAGAAGCTC (25) | 5'-ACTGACTTGGCAGTGCAGATA (26) |
| | FAT | | 5'-TCTCTGAGCTCCTTCCAGTC (27) | 5'-TGGCGTTTGGATCTGCTGAG (28) |
| COBRA and Bisulfite Seqencing | MTNR1A | Region 1 | 5'-GTTAGGTGATATTTGGTGTT (29) | 5'-CATTTAATCCCAAACAACCTA (30) |
| | | Region 2 | 5'-GAGGTTGTTTAGGATGTTTA (31) | 5'-AACACCAAATATCACCTAAC (32) |
| | | Region 3 | 5'-AGTGTTTGGGGAAGGTTGGT (33) | 5'-ATAAACATCCTAAACAACCTCCT (34) |

TABLE 3-continued

| Primer sequences used in this study | | | | |
|---|---|---|---|---|
| Method | Target | | Forward primer (SEQ ID NO) | Reverse primer (SEQ ID NO) |
| MSP | MTNR1A-methylated (MSP) | | 5'-CGGTTTTCGTGGTTGGCGT (35) | 5'-GCGAAAAAACGCTACGTCCG (36) |
| | MTNR1A-unmethylated (USP) | | 5'-TGTGGTTTTTGTGGTTGGTGT (37) | 5'-CCACAAAAAAACACTACATCCAA (38) |
| Mutation analysis | MTNR1A | Exon 1 | 5'-GGCCGGGACGCGCACAG (39) | 5'-AGGCGCTGCGTCCGGAG (40) |
| | | Exon 2 | 5'-AATTGTAACAGAAAACCCACTG (41) | 5'-GACCTGGAGAACCAGGATC (42) |
| | | Exon 2-2 | 5'-CTACACCATCGCCGTGGTG (43) | 5'-GAGCGAGGCCTTGCGCAG (44) |

As a result of the analysis, it was found that the FAT gene was expressed in almost all the cell lines and there were no differences between cancer cells and normal cells in terms of the expression of this gene, and that this gene was not preferable as a target of oral squamous-cell carcinoma.

Figure 2B:
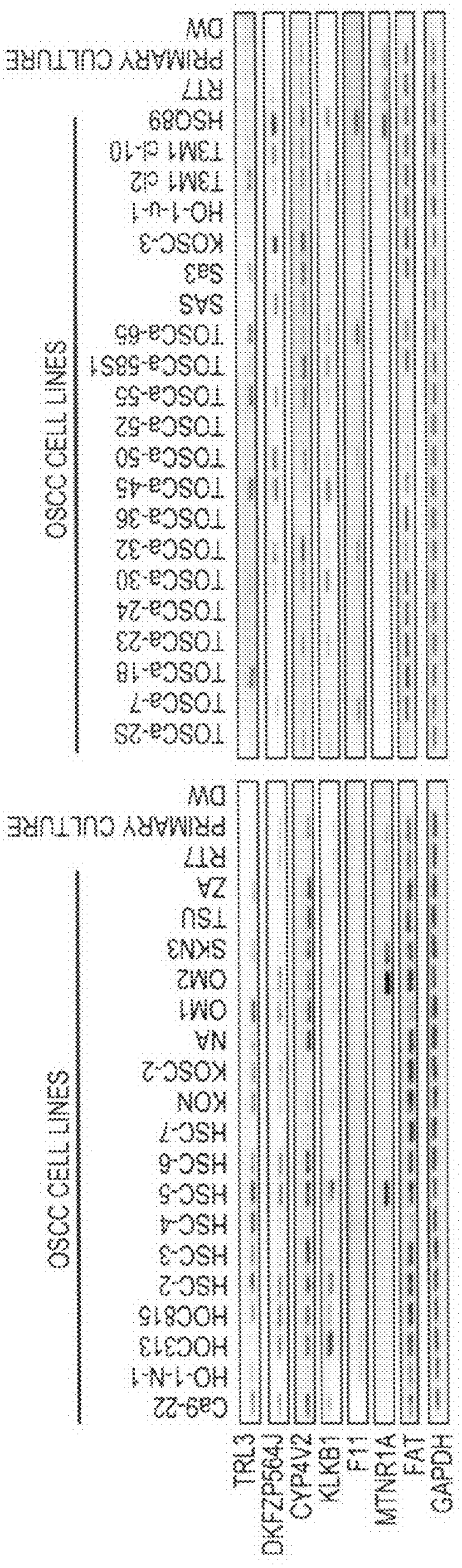

On the other hand, the expression patterns of the CYP4V2 gene, TRL3 gene, DKFZP564J gene, KLKB1 gene and F11 gene were different depending on the types of the cell lines. Although the difference between cancer cells and normal cells was small, it was found that these genes could be used as targets of oral squamous-cell carcinoma (FIG. 2*b*).

Further, when the MTNR1A gene was clearly expressed in the RT7 cells and the primary-cultured epithelial cells from normal oral cavity mucosa, the expression of the mRNA thereof disappeared with a high frequency even in cell lines, in which homozygous deletions were not observed. Thus, it was found that this gene was particularly preferable as a target gene of 4q35 homozygous deletion and inactivation.

Example 4

Recovery of MTNR1A Gene Expression by Demethylation

Figure 2C:
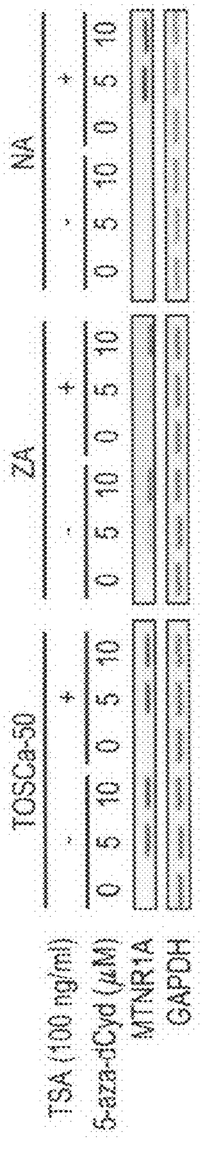

In order to examine if the suppressed expression of the MTNR1A gene was due to DNA methylation, oral squamous-cell carcinoma cell lines (TOSCa-50, ZA, and NA) that had not expressed the MTNR1A gene were treated with a 1 μM or 5 μM demethylating reagent 5-aza-dCyd for 5 days and/or with a deacetylation inhibitory agent TSA (100 ng/ml) for 12 hours. RNAs were extracted from these cells, and MTNR1A gene expression was then examined by RT-PCR (FIG. 2*c*). As a result, it was revealed that the MTNR1A gene recovers its gene expression by treatment with 5-aza-dCyd. It was clearly assumed based on this result that DNA methylation is involved in suppression of the expression of the MTNR1A gene. Moreover, treatment with TSA resulted in no differences in MTNR1A gene expression. Hence, it was revealed that histone deacetylation lightly affects the regulation of MTNR1A gene expression (FIG. 2*c*).

Figure 6A:
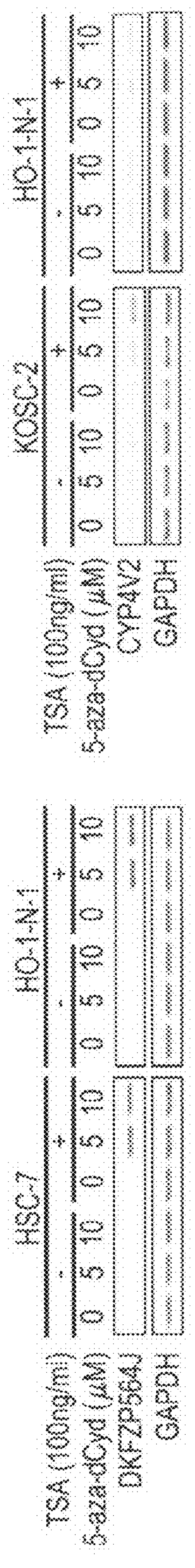
Figure 6B:
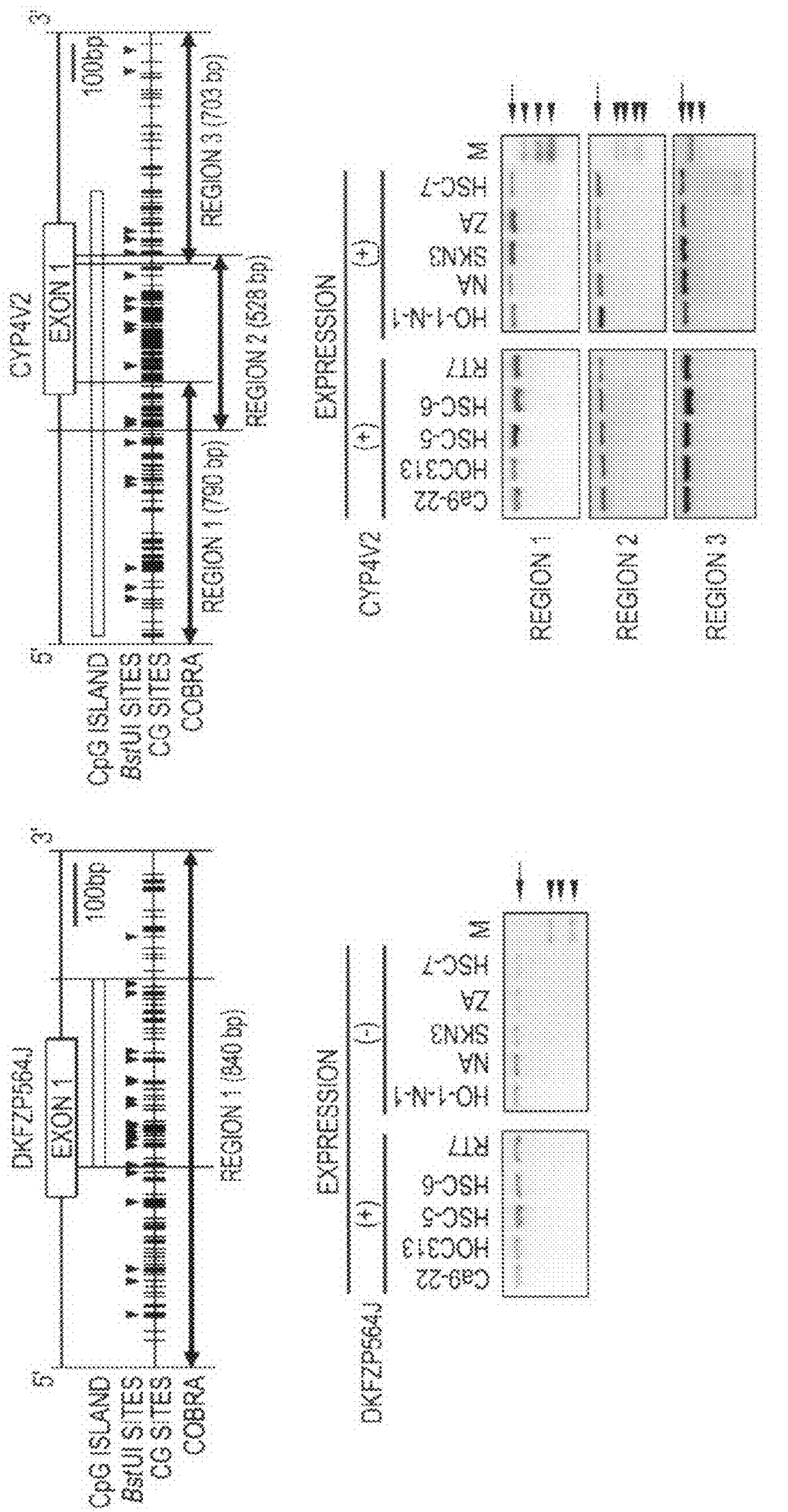

On the other hand, in the case of the CYP4V2 gene and the DKFZP564J gene, gene expression was not recovered by the treatment with 5-aza-dCyd. This result demonstrated that methylation is not involved in inactivation of the CYP4V2 gene and the DKFZP564J gene (FIG. 6).

Example 5

Figure 3A:
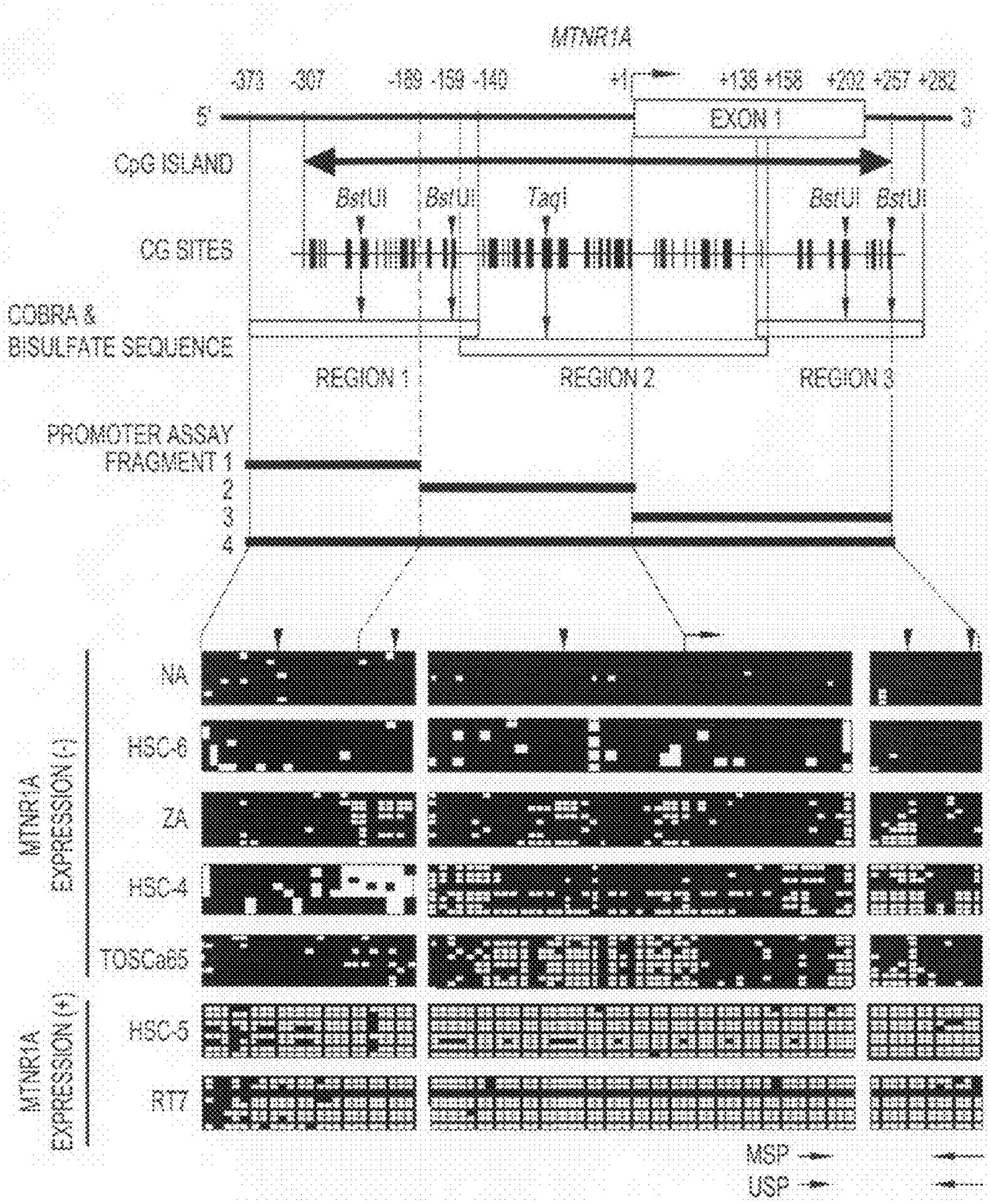

Methylation Status of MTNR1A CpG Island in Oral Squamous-Cell Carcinoma Cell Lines In order to clarify the potential role of the methylation status of CpG island in inactivation of the MTNR1A gene, the degree of methylation of CpG sites around the MTNR1A CpG-islands of the oral squamous-cell carcinoma cell lines (NA, HSC-6, ZA, HSC-4, and TOSCa-65) in which MTNR1A was not expressed, or the oral squamous-cell carcinoma cell line (HSC-5) in which MTNR1A was expressed, and RT7 cells (regions 1-3; FIG. 3*a*), was confirmed by a bisulfite sequence method (Toyota M., et al., Cancer Res. 59, 2307, 1999) (FIG. 3*a*).

As a result, it was revealed that, in the case of the oral squamous-cell carcinoma cell lines (NA, HSC-6, ZA, HSC-4, and TOSCa-65) in which MTNR1A was not expressed, the whole regions were methylated, and that in the case of the oral squamous-cell carcinoma cell line (HSC-5) in which MTNR1A was expressed and RT7 cells, the whole regions were in a low methylation status (FIG. 3*a*).

Further, more cell lines were compared with one another in terms of the relationship between the methylation status and the expression status of the MTNR1A gene according to a Combined bisulfite restriction analysis (COBRA) method (Xiong Z and Laird P. W., Nucleic Acids Res 25: 2532-2534. 1997).

Figure 3B:
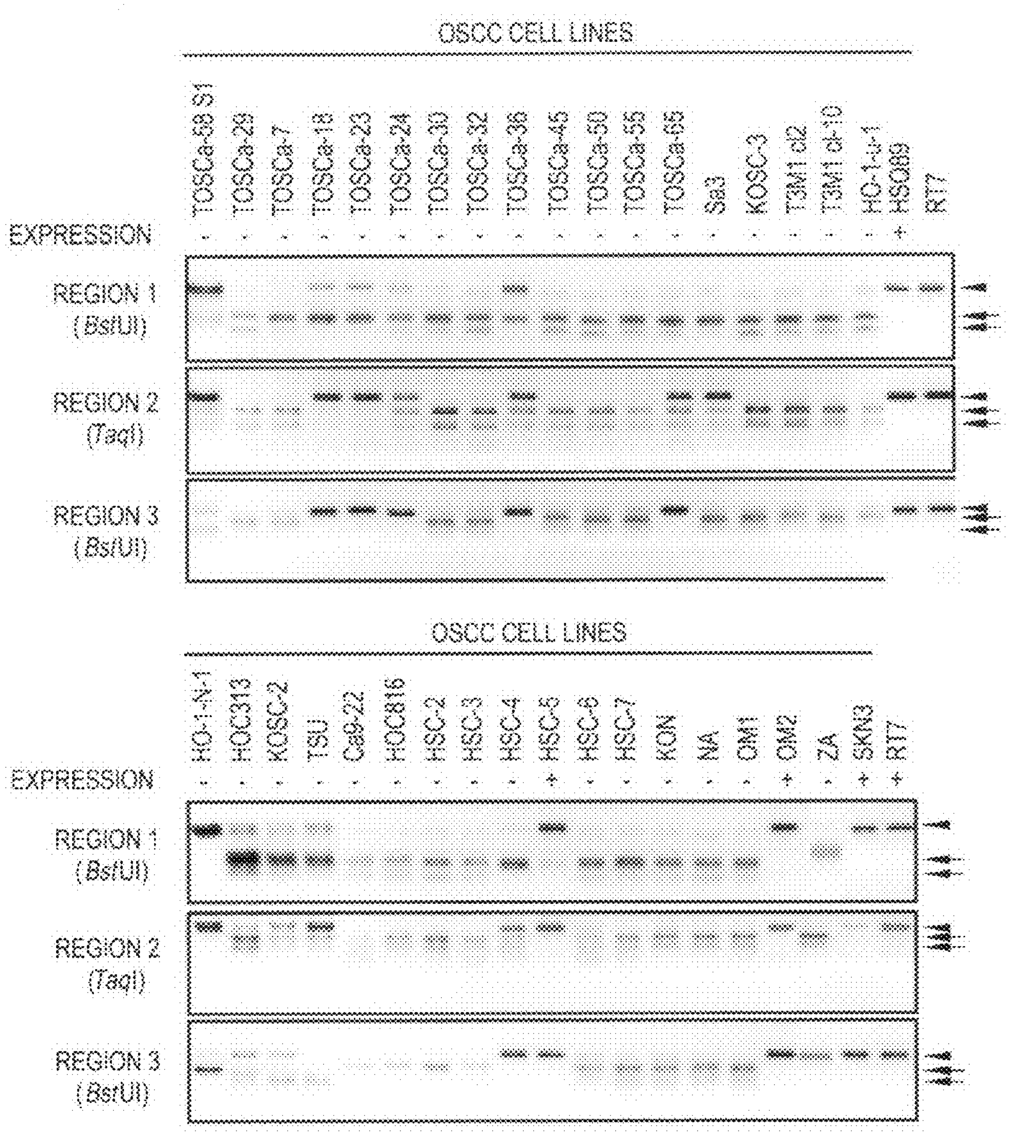

The obtained results corresponded to the results from the aforementioned bisulfite sequence method. That is, unmethylated alleles were mainly detected in cell lines (HSQ89, HSC-5, OM2, and SKN3) in which the MTNR1A gene was expressed and also in the RT cells. In the case of cell lines, which were not attended with homozygous deletion and in which the MTNR1A gene was not expressed, a high level of methylation was observed from the whole regions (FIG. 3*b*).

Example 6

Promoter Activity of MTNR1A CpG Island

Figure 3C:
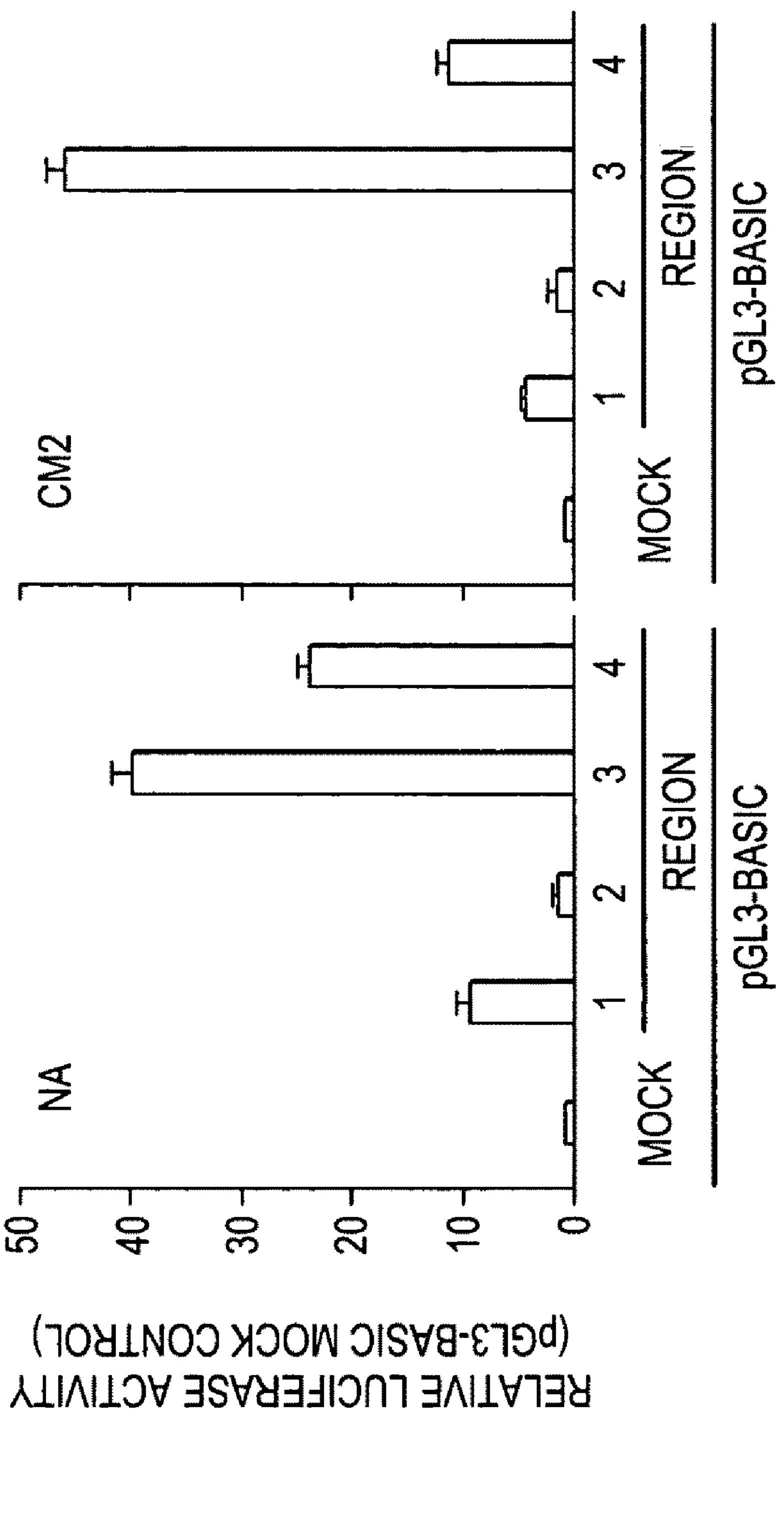

In order to measure promoter activity, two types of squamous-cell carcinoma cells (OM2: MTNR1A-expressed; NA: MTNR1A-not-expressed) were subjected to promoter reporter assay, so as to examine 4 fragment regions that covered putative regions. Specifically, 4 fragments (Fragments 1 to 4) were inserted into luciferase reporter plasmids (pGL3-Basic vector; Promega). Thereafter, the oral squamous-cell carcinoma cell lines (OM2 and NA) were transfected with the plasmids. Luciferase activity was measured according to the manuals using a Dual-Luciferasereporter assay system (Promega). Thus, luciferase activity derived from each pGL3 vector having each fragment was measured (FIG. 3*c*). As a result, it was found that Fragment 3 containing exon 1 and intron 1 existing in regions 2 and 3 has high luciferase activity (FIG. 3*c*). From this result, it was found that Fragment 3 comprises a sequence important for gene inactivation due to methylation.

Example 7

Analysis of Methylation of Promoter Region of MTNR1A Gene in Primary Oral Squamous-Cell Carcinoma Clinical Specimens In order to detect the presence of abnormal methylation in oral squamous-cell carcinoma clinical specimens with higher sensitivity, bisulfite-treated DNA was subjected to an MSP method (methylation-specific PCR method) involving PCR analysis using the primer set described in Table 3, so as to analyze 16 oral squamous-cell carcinoma clinical specimens.

Figure 4A:
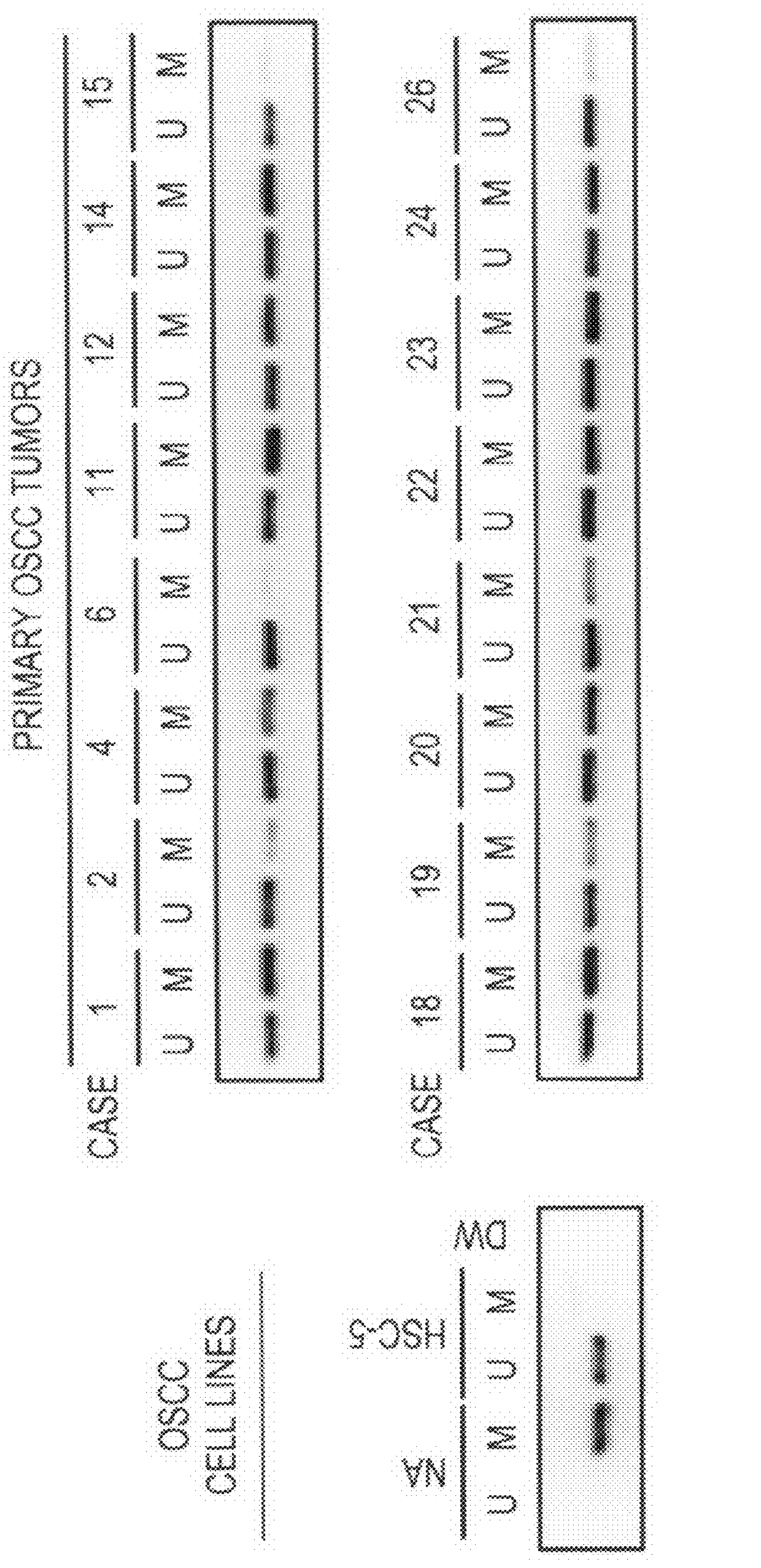
Figure 4B:

As control experiments, it was confirmed that a clear methylation pattern appeared in cells in which the MTNR1A gene was not expressed (NA cells), and that an unmethylation status was observed in cells in which the MTNR1A gene was expressed (HSC-5 cells), as with the analytical results of the bisulfite sequence method and those of the COBRA method. A high level of methylation of the MTNR1A gene was observed in 10 out of the 16 oral squamous-cell carcinoma clinical specimens (FIG. 4*a*). In order to verify the results of the MSP method, the 16 oral squamous-cell carcinoma clinical specimens were subjected to the bisulfite sequence method in the same manner as described above, and it was confirmed that the same results as those of the MSP analysis were obtained (FIG. 4*b*).

Further, the cancerous portions and non-cancerous portions of 6 specimens (clinical specimens 101 to 106) were subjected to the MSP analysis in the same manner as described above. As a result, it was found that the cancerous portions were methylated at a level relatively higher than the non-cancerous portions.

Example 8

Correlation Between Expression Level of MTNR1A Protein and Clinical Background in Oral Squamous-Cell Carcinoma Clinical Specimens In order to reveal the clinical significance of the MTNR1A gene in oral squamous-cell carcinoma clinical specimens, an MTNR1A-specific antibody was used, and the expression level of an MTNR1A protein in oral squamous-cell carcinoma clinical specimens was evaluated by immunohistochemical staining. As a specific method, a paraffin-embedded tissue section was immobilized with formalin. The section on a silane-coated glass slide was subjected to deparaffinization and stepwise dehydration with ethanol. An antigen was obtained by an autoclave pretreatment at 95° C. for 10 minutes in a high pH buffer (Dako Cytomation; Target Retrieval Solution High pH). Endogenous peroxidase was inhibited with the use of 5% hydrogen peroxide. Non-specific staining was inhibited with the use of 2% standard pig serum. The slide was incubated at 4° C. overnight using an anti-human CTGF goat polyclonal antibody (L-20, 1:100 dilution; Santa Cruz Biotechnology). Thereafter, the slide was reacted at room temperature for 2 hours with Histofine simple stain MAX PO (G) (Nichirei). The antigen-antibody reaction was visualized using 0.2% diaminobenzidine tetrahydrochloride and hydrogen peroxide. The resultant slide was counter-stained using Mayer's hematoxylin.

Figure 4C:
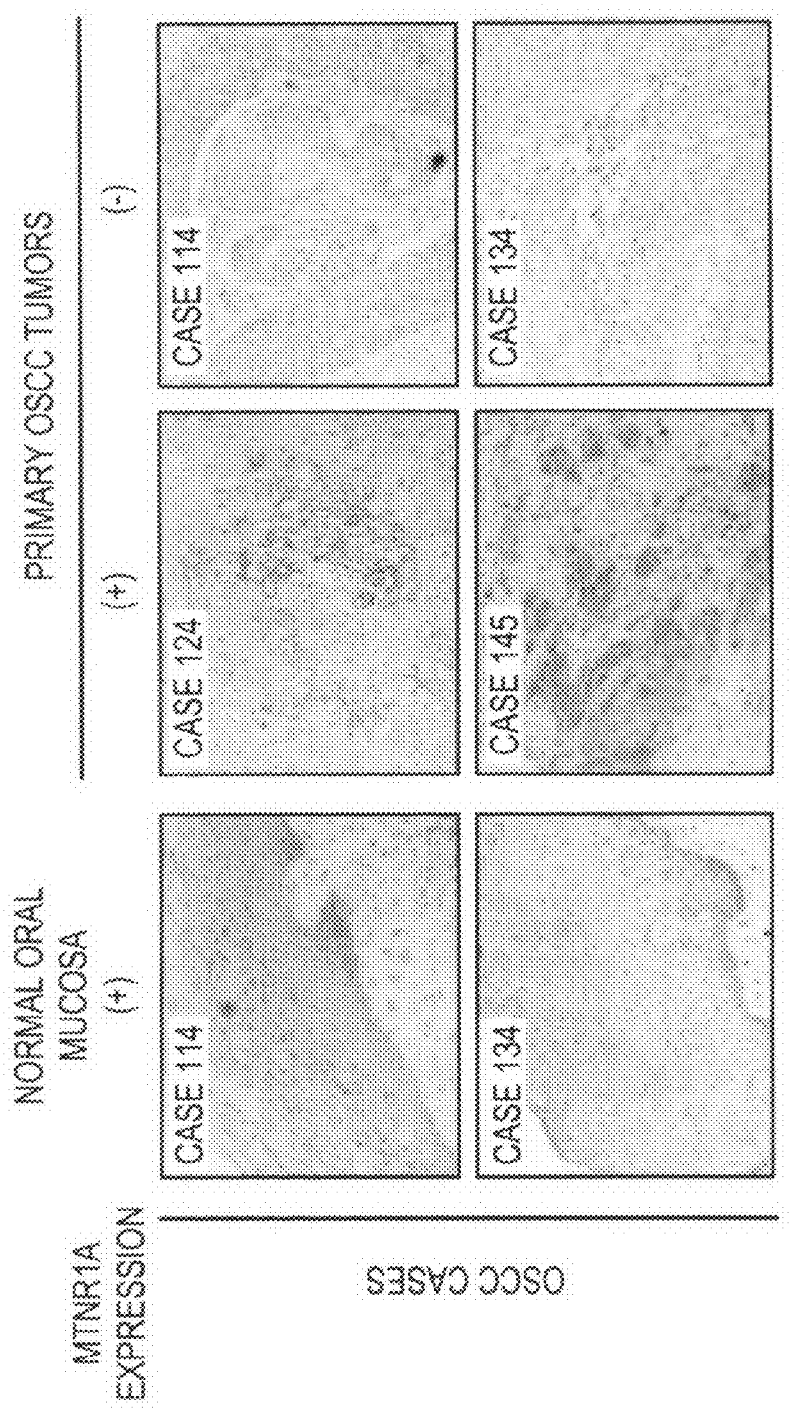
Figure 7A:
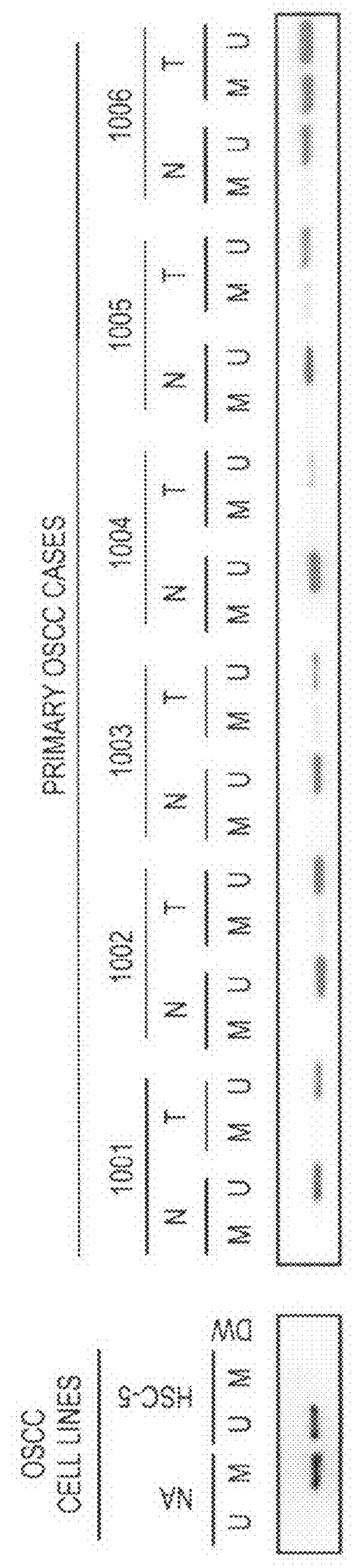
Figure 7B:
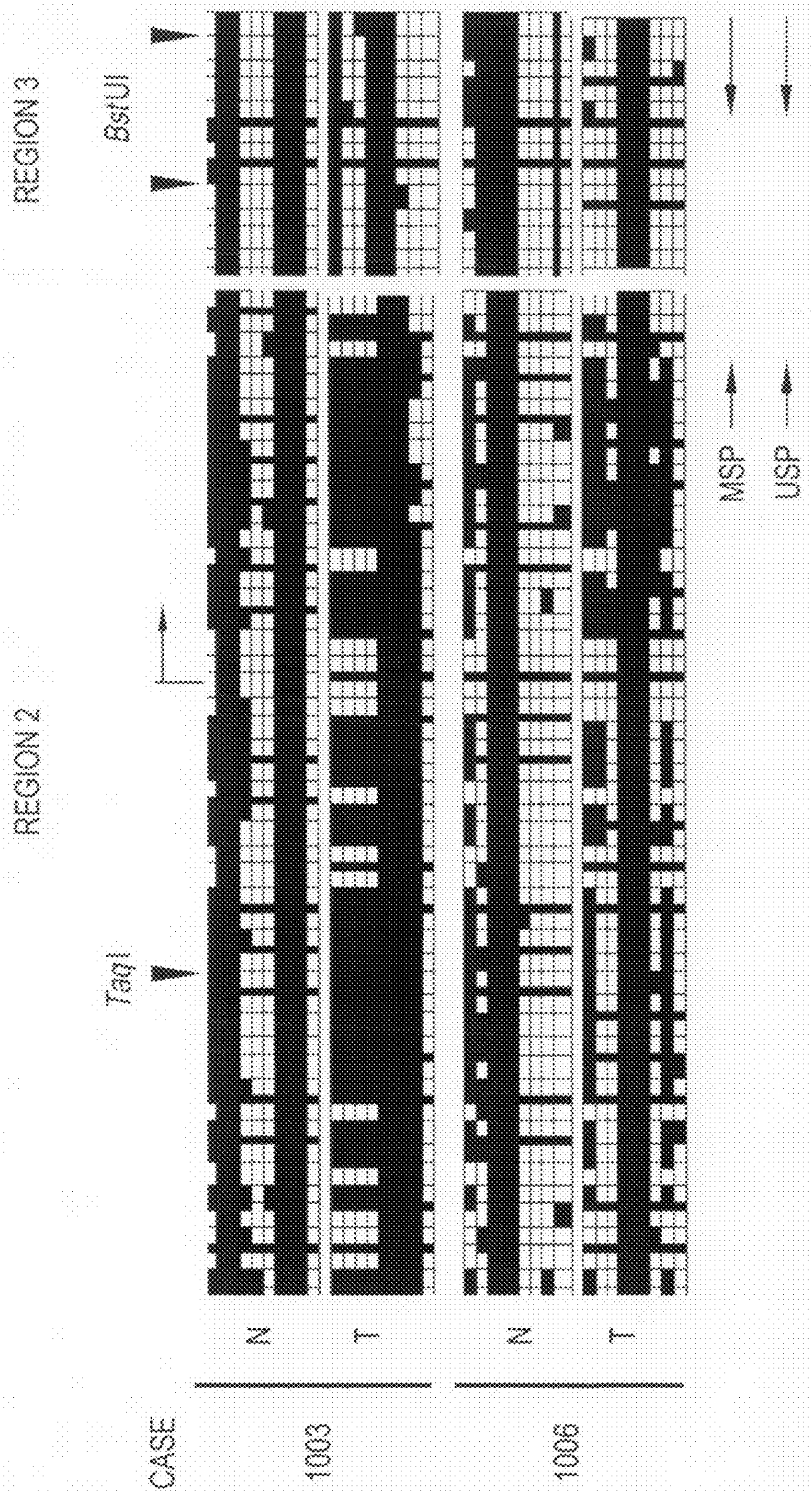
Figure 7C:
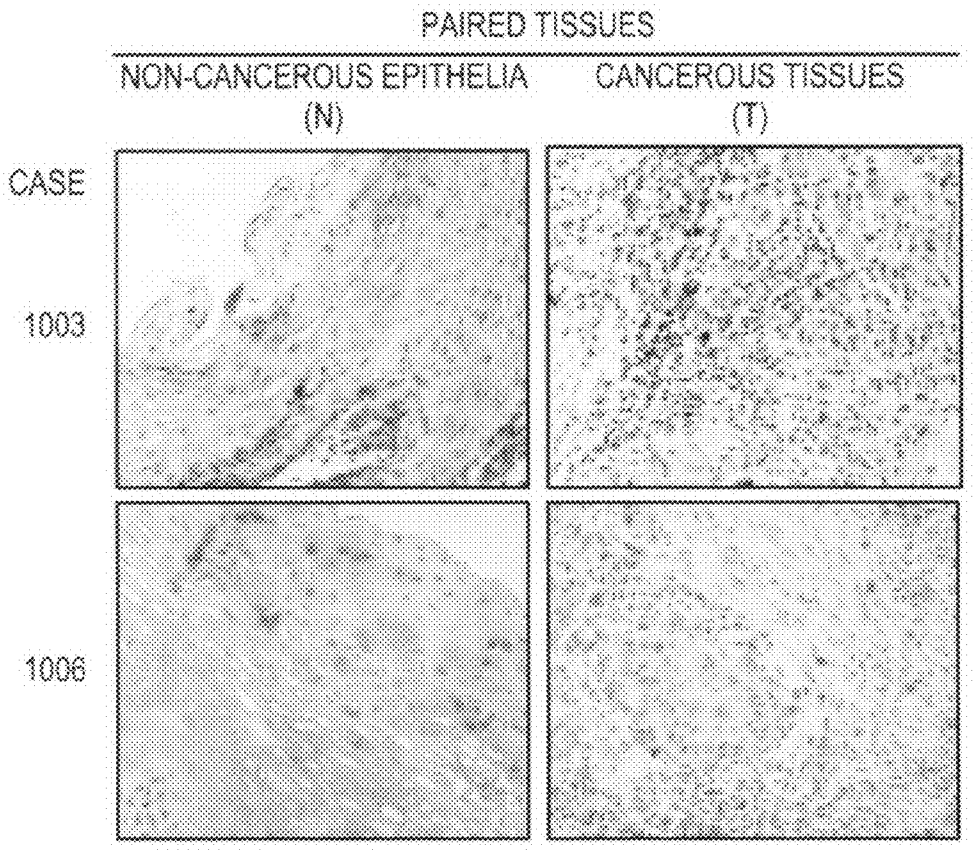

As a result, MTNR1A presented a positive immune response in normal oral mucosal cells. On the other hand, it was revealed that the expression of the MTNR1A protein became inactivated in cancerous portions which were highly methylated in a promoter boundary region, when compared with mucosal cells used as controls (FIG. 4*c* and FIG. 7C).

With regard to 50 types of oral squamous-cell carcinoma clinical specimens, 34 specimens were positive, and 16 specimens were negative. The correlation between the expression of the protein and clinical background is shown in Table 4.

TABLE 4

Correlation between clinical background and expression of MTNR1A protein

| | | MTNR1A expression[a] | | |
|---|---|---|---|---|
| | n | Positive (%) | Negative (%) | P-value[b] |
| Total | **50** | **34** (68) | 16 (32) | |
| Age (years) | | | | |
| <60 | 25 | 18 (72) | 7 (28) | 0.762 |
| ≧60 | 25 | 16 (64) | 9 (36) | |
| Gender | | | | |
| Male | 36 | 22 (61) | 14 (39) | 0.175 |
| Female | 14 | 12 (86) | 2 (14) | |
| Differentiation | | | | |
| Well | 23 | 18 (78) | 5 (22) | 0.258 |
| Poor-Moderate | 27 | 16 (59) | 11 (41) | |
| Stage | | | | |
| I + II | 24 | 18 (75) | 6 (25) | 0.474 |
| III + IV | 26 | 16 (62) | 10 (38) | |
| TNM classification | | | | |
| T stage | | | | |
| T1 + T2 | 36 | **29** (81) | 7 (19) | **0.007** |
| T3 + T4 | 14 | 5 (36) | 9 (64) | |
| N stage | | | | |
| N0 | 32 | **20** (63) | 12 (37) | 0.351 |
| N1-3 | 18 | 14 (78) | 4 (22) | |

NOTE:
Statistically significant values are in boldface type.
[a]MTNR1A expression was evaluated by immunohistochemical analysis as described in Materials and Methods.
[b]P values are from $\chi^2$ or Fisher's exact test and were statistically significant when <0.05 (two sided).

It is found that the expression of the protein significantly correlates with T stage in TNM classification, and that the expression of the MTNR1A protein tends to disappear in tumors at T3 and T4 stages. However, it is also found that the expression of the protein does not correlate with the age and sex of a patient, differentiation degree, stage, and N stage.

Figure 4D:
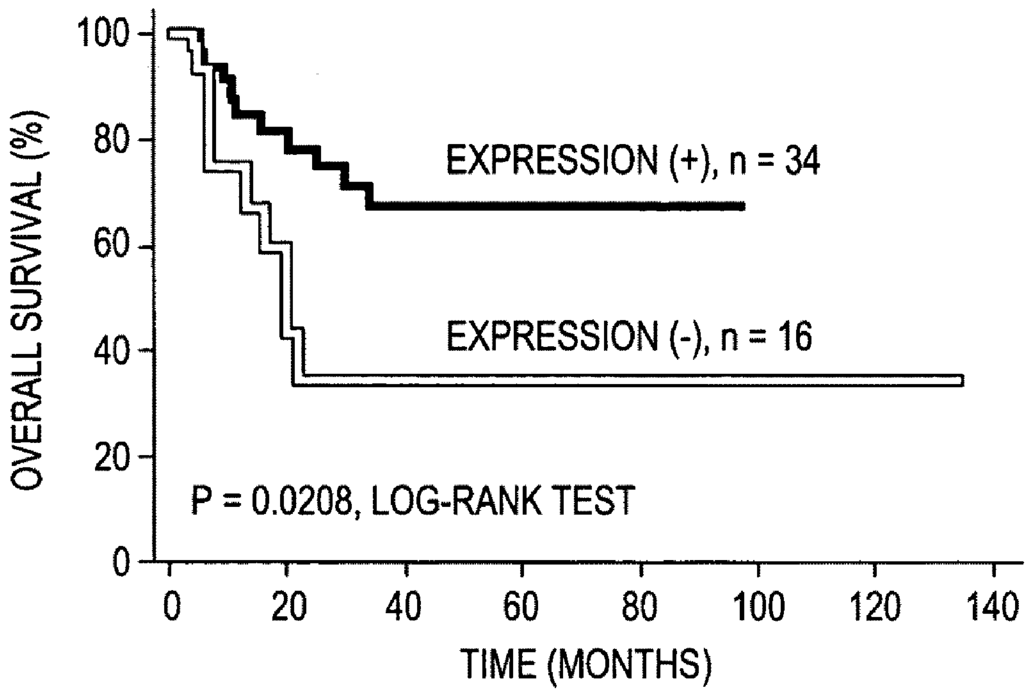

Moreover, it was also found that, in a case where the immune activity of MTNR1A were negative, the overall survival rate was low in all the stages (FIG. 4*d*).

TABLE 5

Cox proportional hazard regression analysis for overall survival

| | Univariate | | |
|---|---|---|---|
| Factor | Hazard ratio (95% confidence interval) | P-value[b] | Multivariate[a] P-value[b] |
| Age (years) | | | |
| ≧60 vs. <60 | 1.060 (0.430-2.612) | 0.899 | — |
| Gender | | | |
| Male vs. Femal | 1.080 (0.410-2.843) | 0.877 | — |
| Diffrentiation | | | |
| Poor-Moderatwe vs. Well | 2.899 (1.041-8.065) | 0.042 | — |

TABLE 5-continued

| Cox proportional hazard regression analysis for overall survival | | | |
| --- | --- | --- | --- |
| | Univariate | | |
| Factor | Hazard ratio (95% confidence interval) | P-value[b] | Multivariate[a] P-value[b] |
| Stage | | | |
| III + IV vs. I + II | 4.184 (1.493-11.765) | 0.007 | **0.0099** |
| TNM classification | | | |
| T stage | | | |
| T3 + T4 vs. T1 + T2 | 3.509 (1.416-8.696) | 0.007 | — |
| N stage | | | |
| N1-3 vs. N0 | 2.193 (0.890-5.405) | 0.088 | — |
| MTNR1A expression[c] | | | |
| Negative vs. Positive | 2.816 (1.128-7.029) | 0.027 | **0.0498** |

NOTE:

Statistically significant values are in boldface type.

[a]Forward- and backward-stepwise analyses were used for multivariate analysis.

[b]P-values are from two-sided tests and were statistically significant when <0.05.

[c]MTNR1A expression was evaluated by immunohistochemical analysis as described in Materials and Methods.

Example 9

Confirmation of Effect of MTNR1A Gene to Suppress Growth of OCSS Cell Line

Figure 5A:
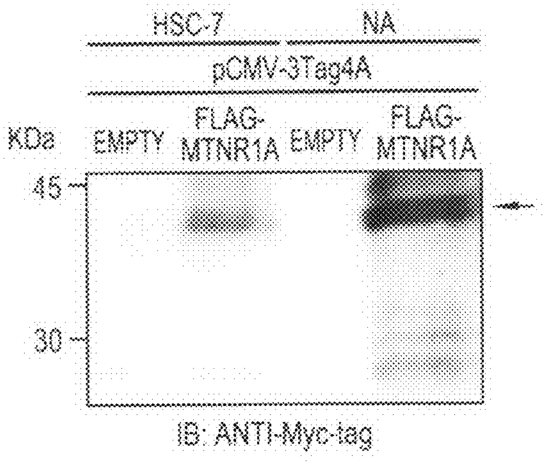

Taking into consideration the obtained results, whether or not the growth of OSCC cells is suppressed by activation of the MTNR1A gene expression was analyzed. First, a plasmid expressing the Myc tag of the MTNR1A gene (pCMV-3Tag4A-FLAG-MTNR1A) was constructed. This plasmid was produced by inserting the cDNA of MTNR1A amplified by RT-PCR into a pCMV-3Tag4A vector (Stratagene) such that the Myc tag matched the translation frame. An empty vector (pCMV-3Tag4A-mock) into which no ITCH gene had been inserted was used as a control. These expression plasmids were mixed with a transfection reagent, Lipofectamine 2000 (Invitrogen). Thereafter, HSC-7 cells and NA cells were transfected with the plasmids. The cells were recovered after 24 hours and were then subjected to Western blot analysis using ProteoExtract Transmembrane Protein Extraction Kit (Novagen) and an anti-Myc antibody (Cell Signaling Technology). Thus, the MTNR1A protein expression was confirmed (FIG. 5A).

On 2 weeks after the transfection, the cells that had proliferated in the presence of a neomycin-based agent, G418, were fixed with 70% ethanol, were stained with crystal violet, and were then counted.

Figure 5B:
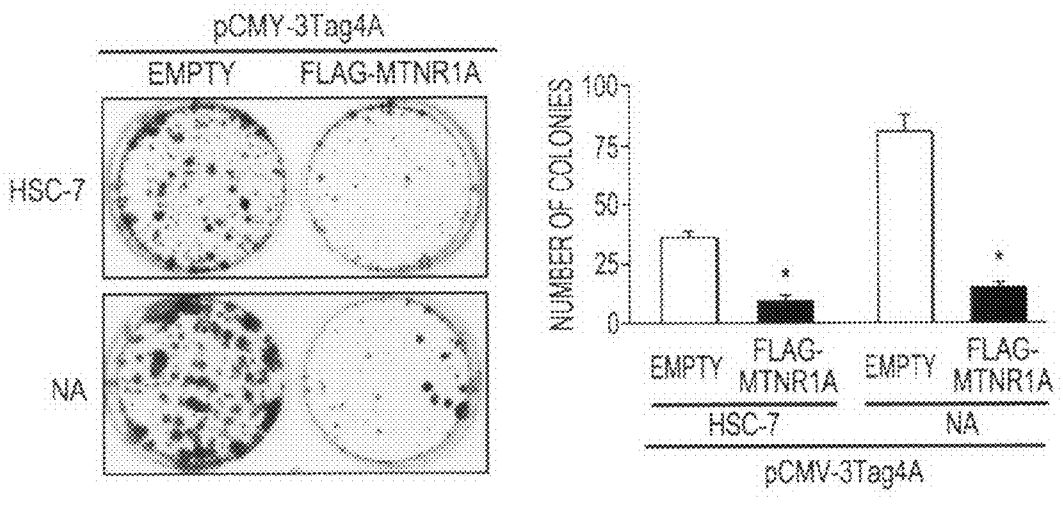

As a result, the colony number of the cells transfected with pCMV-3Tag4A-FLAG-MTNR1A significantly decreased, when compared with that of the cells transfected with the empty vector (FIG. 5*b*). The results clearly demonstrate that the proliferation of OSCC cells can be suppressed through activation of the MTNR1A gene expression.

The invention claimed is:

1. A method for detecting oral squamous-cell carcinoma in a patient, which comprises detecting deletion of a MTNR1A gene or hypermethylation of the MTNR1A gene in an oral-cavity-derived cell from the patient, wherein deletion of the MTNR1A gene or hypermethylation of the MTNR1A gene in an oral-cavity-derived cell from the patient is indicative of oral squamous-cell carcinoma.

2. The method for detecting oral squamous-cell carcinoma in a patient according to claim 1, wherein deletion of the MTNR1A gene or hypermethylation of the MTNR1A gene in the oral-cavity-derived cell from the patient is detected using a DNA chip method, a Southern blot method, a Northern blot method, a real-time RT-PCR method, a FISH method, a CGH method, an array CGH method, a bisulfite sequencing method, or a COBRA method.

* * * * *

SEQUENCE LISTING

```
<160> NUMBER OF SEQ ID NOS: 44

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1

gcagcatata taattcatg                                                  19


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2

tgatgctgtt aacaattgct                                                 20


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
```

-continued

<400> SEQUENCE: 3
tcacaatatg tgcctaaatc 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 4
cacagataaa tataacactt 20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic DNA

<400> SEQUENCE: 5
tccaggagaa agatgttaac ac 22

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic DNA

<400> SEQUENCE: 6
cagatgatat ctaaggcac 19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 7
gtggtccctt agtttgcaaa c 21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic DNA

<400> SEQUENCE: 8
actgcatctg agcttttcca tc 22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 9
catctggtag gcatcacgag 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 10
ctgggaaccc attcacactg 20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 11
gaaacatctt tgtggtg 17

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 12
actgacttgg cagtgcagat a 21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 13
tagagaagtg aaggatcact ac 22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 14
ggtgggtgag aataacggtc 20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
DNA -continued

<400> SEQUENCE: 15
aatccctttg tcaagcagaa g 21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic DNA

<400> SEQUENCE: 16
ttgataatag aagctcttgg ag 22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 17
atgagaagga ggacaaagca 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 18
gctccgtgac gtttgaacca 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 19
atacaactgc agctgcaata 20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 20
ggtctcctta ataacacatt c 21

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic DNA

<400> SEQUENCE: 21
atggggcttc tcgaaggag 19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic DNA

<400> SEQUENCE: 22
cagcacagac catccgttg 19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 23
ccagaagaga tacagaggac a 21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 24
ctcgtgatgc ctaccagatg 20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic DNA

<400> SEQUENCE: 25
ggtgtatcgg aacaagaagc tc 22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 26
actgacttgg cagtgcagat a 21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 27
tctctgagct ccttccagtc 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 28
tggcgtttgg atctgctgag 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 29
gttaggtgat atttggtgtt 20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 30
catttaatcc caaacaacct a 21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 31
gaggttgttt aggatgttta 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 32
aacaccaaat atcacctaac 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 33
agtgtttggg gaaggttggt 20

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic DNA

<400> SEQUENCE: 34
ataaacatcc taaacaacct cct 23

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic DNA

<400> SEQUENCE: 35
cggttttcgt ggttggcgt 19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 36
gcgaaaaaac gctacgtccg 20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 37
tgtggttttt gtggttggtg t 21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic DNA

<400> SEQUENCE: 38
ccacaaaaaa acactacatc caa 23

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic DNA -continued

<400> SEQUENCE: 39
ggccgggacg cgcacag 17

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 40
aggcgctgcg tccggag 17

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 41
aattgtaaca gaaaacccac tg 22

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 42
gacctggaga accaggatc 19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 43
ctacaccatc gccgtggtg 19

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 44
gagcgaggcc ttgcgcag 18